United States Patent
Lee et al.

(10) Patent No.: US 8,110,547 B2
(45) Date of Patent: Feb. 7, 2012

(54) COMPOSITIONS FOR BUCCAL DELIVERY OF PARATHYROID HORMONE

(75) Inventors: Jongbin Lee, New City, NY (US);
Puchun Liu, Chappaqua, NY (US);
Steven Dinh, Briarcliff Manor, NY (US)

(73) Assignee: Emisphere Technologies, Inc., Cedar Knolls, NJ (US)

( * ) Notice: Subject to any disclaimer, the term of this patent is extended or adjusted under 35 U.S.C. 154(b) by 150 days.

(21) Appl. No.: 11/813,700

(22) PCT Filed: Jan. 12, 2006

(86) PCT No.: PCT/US2006/001445
§ 371 (c)(1),
(2), (4) Date: Feb. 26, 2008

(87) PCT Pub. No.: WO2006/076692
PCT Pub. Date: Jul. 20, 2006

(65) Prior Publication Data
US 2008/0200380 A1    Aug. 21, 2008

Related U.S. Application Data

(60) Provisional application No. 60/643,523, filed on Jan. 12, 2005.

(51) Int. Cl.
*A61K 38/29* (2006.01)
(52) U.S. Cl. .............. 514/11.8; 514/16.7; 514/16.9
(58) Field of Classification Search ............ None
See application file for complete search history.

(56) References Cited

U.S. PATENT DOCUMENTS

| | | | |
|---|---|---|---|
| 5,536,749 A * | 7/1996 | Matier et al. | 514/533 |
| 5,814,603 A * | 9/1998 | Oldenburg et al. | 514/12 |
| 5,849,322 A * | 12/1998 | Ebert et al. | 424/435 |
| 5,866,536 A | 2/1999 | Leone-Bay et al. | |
| 5,876,710 A | 3/1999 | Leone-Bay et al. | |
| 5,879,681 A | 3/1999 | Leone-Bay et al. | |
| 5,935,601 A | 8/1999 | Leone-Bay et al. | |
| 5,939,381 A | 8/1999 | Leone-Bay et al. | |
| 5,955,503 A | 9/1999 | Leone-Bay et al. | |
| 5,958,451 A | 9/1999 | Chen | |
| 5,962,710 A | 10/1999 | Gschneidner et al. | |
| 5,965,121 A | 10/1999 | Leone-Bay et al. | |
| 5,972,387 A | 10/1999 | Milstein et al. | |
| 5,976,569 A | 11/1999 | Milstein | |
| 5,989,539 A | 11/1999 | Leone-Bay et al. | |
| 5,990,166 A | 11/1999 | Leone-Bay et al. | |

(Continued)

FOREIGN PATENT DOCUMENTS

WO    WO9612475 A1    5/1996
(Continued)

OTHER PUBLICATIONS

Leone-Bay et al. Oral Delivery of Biologically Active Parathyroid Hormone. Pharmaceutical Research. 2001, vol. 18, No. 7, pp. 964-970.*

(Continued)

*Primary Examiner* — Jeffrey E Russel
(74) *Attorney, Agent, or Firm* — Blank Rome LLP

(57) ABSTRACT

Compositions and pharmaceutical formulations for buccally delivering parathyroid hormone comprising a) a delivery agent, b) a PTH component and, optionally, c) an antiresorptive agent are provided.

11 Claims, 7 Drawing Sheets

-♦- 0.2 mg/kg hPTH(1-34) without a delivery agent (n=5)
-▲- 0.2 mg/kg hPTH(1-34) with 200 mg/kg monosodium 4-MOAC (n=12)
-◊- 0.2 mg/kg hPTH(1-34) with 200 mg/kg monosodium SNAD (n=6)
-□- 0.2 mg/kg hPTH(1-34) with 200 mg/kg monosodium 4-CNAB (n=6)

Dosing Duration: 90 minutes

U.S. PATENT DOCUMENTS

| | | | |
|---|---|---|---|
| 6,001,347 A | 12/1999 | Leone-Bay et al. |
| 6,051,258 A | 4/2000 | Kantor |
| 6,051,561 A | 4/2000 | Leone-Bay et al. |
| 6,060,513 A | 5/2000 | Leone-Bay et al. |
| 6,071,510 A | 6/2000 | Leone-Bay et al. |
| 6,084,112 A | 7/2000 | Ho et al. |
| 6,090,958 A | 7/2000 | Leone-Bay et al. |
| 6,099,856 A | 8/2000 | Milstein et al. |
| 6,100,285 A | 8/2000 | Kantor |
| 6,100,298 A | 8/2000 | Leone-Bay et al. |
| 6,180,140 B1 | 1/2001 | Leone-Bay et al. |
| 6,221,367 B1 | 4/2001 | Milstein et al. |
| 6,242,495 B1 | 6/2001 | Leone-Bay et al. |
| 6,245,359 B1 | 6/2001 | Milstein et al. |
| 6,313,088 B1 | 11/2001 | Leone-Bay et al. |
| 6,331,318 B1 | 12/2001 | Milstein |
| 6,344,213 B1 | 2/2002 | Leone-Bay et al. |
| 6,346,242 B1 | 2/2002 | Leone-Bay et al. |
| 6,358,504 B1 | 3/2002 | Leone-Bay et al. |
| 6,375,983 B1 | 4/2002 | Kantor et al. |
| 6,440,929 B1 | 8/2002 | Milstein et al. |
| 6,461,545 B1 | 10/2002 | Kantor |
| 6,461,643 B2 | 10/2002 | Milstein et al. |
| 6,525,020 B2 | 2/2003 | Leone-Bay et al. |
| 6,558,706 B2 | 5/2003 | Kantor et al. |
| 6,610,329 B2 | 8/2003 | Santiago et al. |
| 6,623,731 B2 | 9/2003 | Leone-Bay et al. |
| 6,627,228 B1 | 9/2003 | Milstein et al. |
| 6,642,411 B1 | 11/2003 | Leone-Bay et al. |
| 6,646,162 B2 | 11/2003 | Tang et al. |
| 6,663,887 B2 | 12/2003 | Leone-Bay et al. |
| 6,663,898 B2 | 12/2003 | Milstein et al. |
| 6,693,073 B2 | 2/2004 | Milstein et al. |
| 6,693,208 B2 | 2/2004 | Gscheidner et al. |
| 6,693,898 B1 | 2/2004 | Su et al. |
| 6,699,467 B2 | 3/2004 | Leone-Bay et al. |
| 2002/0065255 A1* | 5/2002 | Bay et al. ............... 514/166 |
| 2003/0059376 A1* | 3/2003 | Libbey et al. ............. 424/46 |
| 2003/0219472 A1* | 11/2003 | Pauletti et al. ............ 424/449 |
| 2004/0048777 A1* | 3/2004 | Weidner et al. ............ 514/2 |
| 2005/0054557 A1* | 3/2005 | Goldberg ................ 514/2 |

FOREIGN PATENT DOCUMENTS

| | | |
|---|---|---|
| WO | WO9621464 A1 | 7/1996 |
| WO | WO9630036 A1 | 10/1996 |
| WO | WO9633699 A1 | 10/1996 |
| WO | WO9639835 A1 | 12/1996 |
| WO | WO9640070 A1 | 12/1996 |
| WO | WO9640076 A1 | 12/1996 |
| WO | WO9710197 A1 | 3/1997 |
| WO | WO9731938 A1 | 9/1997 |
| WO | WO9747288 A1 | 12/1997 |
| WO | WO9821951 A1 | 5/1998 |
| WO | WO9825589 A1 | 6/1998 |
| WO | WO9834632 A1 | 8/1998 |
| WO | WO9849135 A1 | 11/1998 |
| WO | WO9850341 A1 | 11/1998 |
| WO | WO0006184 A1 | 2/2000 |
| WO | WO0006534 A1 | 2/2000 |
| WO | WO0007979 A3 | 2/2000 |
| WO | WO9916427 A1 | 4/2000 |
| WO | WO0040203 A3 | 7/2000 |
| WO | WO0046182 A1 | 8/2000 |
| WO | WO0047188 A1 | 8/2000 |
| WO | WO0048589 A1 | 8/2000 |
| WO | WO0050386 A1 | 8/2000 |
| WO | WO0059480 A1 | 10/2000 |
| WO | WO0059863 A1 | 10/2000 |
| WO | WO0132130 A3 | 5/2001 |
| WO | WO0132596 A1 | 5/2001 |
| WO | WO0134114 A1 | 5/2001 |
| WO | WO0144199 A1 | 6/2001 |
| WO | WO0151454 A1 | 7/2001 |
| WO | WO0170219 A1 | 9/2001 |
| WO | WO0192206 A1 | 12/2001 |
| WO | WO0202509 A2 | 2/2002 |
| WO | WO0215969 A1 | 2/2002 |
| WO | WO0216309 A1 | 3/2002 |
| WO | WO0219969 A2 | 3/2002 |
| WO | WO0220466 A1 | 3/2002 |
| WO | WO02069937 A1 | 9/2002 |
| WO | WO02070438 A2 | 9/2002 |
| WO | WO 03015822 A1 * | 2/2003 |
| WO | WO03026582 A2 | 4/2003 |
| WO | WO03045306 A3 | 6/2003 |
| WO | WO03045331 A2 | 6/2003 |
| WO | WO03057170 A2 | 7/2003 |
| WO | WO03057650 A2 | 7/2003 |
| WO | WO02100338 A3 | 12/2003 |
| WO | WO2004104018 A | 2/2004 |
| WO | WO2004062587 A2 | 7/2004 |
| WO | WO2004080401 A2 | 9/2004 |

OTHER PUBLICATIONS

U.S. Appl. No. 60/569,475, filed May 6, 2004, Emisphere Technologies, Inc.

T.W. Greene, "Protective Groups in Organic Synthesis," Wiley, New York. (1981).

"Remington : The Science and Practice of Pharmacy," (Gennaro, A.R., ed., 20th edition, 2003, Mack Pub. Co.).

"Handbook of Pharmaceutical Excipients," published by the American Pharmaceutical Association and the Pharmaceutical Society of Great Britain. (1986).

"Handbook of Water-Soluble Gums and Resins," ed. by R.L. Davidson, McGraw-Hill Book Co., New York, N.Y. (1980).

* cited by examiner

-♦- 0.2 mg/kg hPTH(1-34) without a delivery agent (n=5)

-▲- 0.2 mg/kg hPTH(1-34) with 200 mg/kg mononsodium 4-MOAC (n=12)

-◊- 0.2 mg/kg hPTH(1-34) with 200 mg/kg monosodium SNAD (n=6)

-□- 0.2 mg/kg hPTH(1-34) with 200 mg/kg monosodium 4-CNAB (n=6)

Dosing Duration: 90 minutes

-♦- 0.05 mg/kg hPTH(1-34) with 50 mg/kg 4-MOAC (n=10)

-■- 0.05 mg/kg hPTH(1-34) with 100 mg/kg monosodium 4-MOAC (n=10)

-△- 0.05 mg/kg hPTH(1-34) with 200 mg/kg monosodium 4-MOAC (n=10)

Dosing Duration: 5 minutes

-♦- 0.2 mg/kg hPTH(1-34) with 200 mg/kg monosodium 4-MOAC (n=10)

-■- 0.2 mg/kg hPTH(1-34) with 100 mg/kg monosodium 4-MOAC (n=10)

-○- 0.2 mg/kg hPTH(1-34) with 50 mg/kg monosodium 4-MOAC (n=10)

Dosing Duration: 5 minutes

-▲- 0.3 mg/kg hPTH(1-34) with 100 mg/kg monosodium 4-MOAC (n=10)

-■- 0.2 mg/kg hPTH(1-34) with 100 mg/kg monosodium 4-MOAC (n=10)

-Δ- with 0.1 mg/kg hPTH(1-34) with 100 mg/kg monosodium 4-MOAC (n=10)

--- 0.05 mg/kg hPTH(1-34) with 100 mg/kg monosodium 4-MOAC (n=10)

Dosage Duration: 5 minutes 0.2 mg/kg hPTH(1-34) with 200 mg/kg monosodium 4-MOAC over a dosing duration of:

-△- 2 minutes (n=7)

-◆- 5 minutes (n=20)

-□- 15 minutes (n=7)

-▲- 60 minutes (n=20)

-■- buccal administration of 0.2 mg/kg hPTH(1-34) with 200 mg/kg monosodium 4-MOAC for a dosing duration of 60 minutes (n=20)

-△- oral administration of 0.2 mg/kg hPTH(1-34) with 200 mg/kg monosodium 4-MOAC (n=10)

-♦- buccal administration of 0.2 mg/kg hPTH(1-34) with 200 mg/kg monosodium 4-MOAC for a dosing duration of 5 minutes (n=10)

-△- oral administration of 0.2 mg/kg PTH with 200 mg/kg monosodium 4-MOAC (n=10)

COMPOSITIONS FOR BUCCAL DELIVERY OF PARATHYROID HORMONE

This application is a U.S. national stage of PCT Application No. PCT/US2006/001445, filed Jan. 12, 2006, claims the benefit of U.S. Provisional Application No. 60/643,523, filed Jan. 12, 2005, which is hereby incorporated by reference in its entirety.

FIELD OF THE INVENTION

The present invention relates to buccal delivery of parathyroid hormone or a fragment or an analog thereof (collectively, the "PTH component") with a delivery agent, pharmaceutical compositions for buccal administration comprising a PTH component and a delivery agent, and methods of preventing or treating osteoporosis or stimulating new bone formation in an animal by buccally co-administering a PTH component and a delivery agent.

BACKGROUND OF THE INVENTION

Osteoporosis is a skeletal disorder characterized by compromised bone strength predisposing an individual to an increased risk of fracture. Osteoporosis affects 20 million people in the United States and leads to an estimated 1.2 million bone fractures annually. It has been estimated that approximately 30 percent of all post-menopausal Caucasian women will suffer from an osteoporotic fracture. Osteoporosis may be treated and/or prevented using a number of different active agents such as antiresorptive agents (e.g., estrogen, selective estrogen receptor modulators, bisphosphonates, and calcitonin) or anabolic agents (e.g., parathyroid hormone). Antiresorptive agents impart skeletal benefits by reducing osteoclastic resorption of bone, thus causing a reduction in bone remodeling and an increase in bone mineral density (BMD). Anabolic agents generally reduce risk of osteoporotic fracture by stimulating new bone formation.

Human parathyroid hormone is a naturally occurring protein that is secreted as a linear 84 amino acid peptide. Parathyroid hormone regulates calcium concentration in the blood stream by stimulating osetoclasts to reabsorb calcium from bone, enhancing calcium absorption from the small intestine and suppressing calcium loss in the urine. Hock et al., *J. Bone Miner. Res* 4:449-458 (2002). Synthetic parathyroid hormones have been developed as medicaments to enhance the uptake of calcium and to stimulate new bone formation. One recombinant parathyroid hormone is Forteo® (teriparatide (rDNA origin), recombinant human parathyroid hormone (1-34)) (available from Eli Lilly and Company of Indianapolis, Ind.). Forteo® is administered by subcutaneous injection for (1) the treatment of postmenopausal women with osteoporosis who are at high risk for fracture, and (2) to increase bone mass in men with primary or hypogonadal osteoporosis who are at high risk for fracture.

The medical condition, hypoparathyroidism may have a number of divergent causes. For example, removal of the parathyroid glands in thyroid surgery (thyroidectomy) is a recognized cause. It is now uncommon, as surgeons generally spare them during the procedure after identifying them. Autoimmune invasion and destruction is the most common non-surgical cause. It can occur as part of autoimmune polyendocrine syndromes. Hemochromatosis can lead to iron accumulation and consequent dysfunction of a number of endocrine organs, including the parathyroids. Absence or dysfunction of the parathyroid glands is one of the components of chromosome 22q11 microdeletion syndrome (other names: DiGeorge syndrome, Schprintzen syndrome, velocardiofacial syndrome). Magnesium deficiency, some very rare diseases and idiopathic (of unknown cause), occasionally familial causes lead to hypoparathyroidism.

The physiologic function of PTH is the maintenance of sufficient calcium levels. This is achieved by bone resorption, renal reabsorption of calcium (in the distal tubule) and Vitamin D3 (1,25—OH-D3) synthesis (also in the kidney) from Vitamin D1 (25—OH-D3).

Severe hypocalcemia, a potentially life-threatening condition, is treated as soon as possible with intravenous calcium. Long-term treatment of hypoparathyroidism is with calcium and vitamin D3 supplementation (D1 is ineffective in the absence of renal conversion). A synthetic or naturally derived form of PTH, such as in the present invention, might become the treatment of choice for PTH supplementation in patients with hyperparathyroidism.

Buccal delivery is a more preferable method of administering drugs and offers several advantages over subcutaneous injection. Typically, a buccal dosage form is placed in the buccal cavity between the gum and the cheek, where it dissolves in the patient's saliva, releasing the drug into the buccal cavity in close proximity to the capillary bed of the oral mucosa. The drug then enters the blood in the capillary bed by diffusion through the mucosal tissue and is distributed in the bloodstream to the rest of the body.

Buccal administration is less invasive and results in greater patient compliance compared to subcutaneous injection. Furthermore, unlike oral administration, buccal administration avoids the possibility that the drug will be destroyed in the gastrointestinal tract before it can be absorbed, and eliminates first-pass inactivation in the liver after absorption.

Therefore, there is a need for a parathyroid hormone formulation which can be buccally administered.

SUMMARY OF THE INVENTION

The present invention relates to a pharmaceutical composition for buccal administration comprising (a) a delivery agent and (b) (i) parathyroid hormone (PTH) or a fragment thereof (such as fragments of human parathyroid hormone which include its first 28 amino acids) or an analog thereof (collectively, the "PTH component"), and optionally (ii) an antiresorptive agent (such as a bisphosphonate, estrogen, selective estrogen receptor modulators, calcitonin, Vitamin D, or a mixture thereof). The pharmaceutical composition of the present invention may be formulated into a dosage unit form, such as a buccal dosage unit form.

Another embodiment is a method for administering a PTH component to an animal or patient (such as an animal or patient in need thereof) by buccally co-administering a delivery agent and the PTH component. Preferably, a pharmaceutical composition or unitary dosage form containing both is administered. Preferably, a therapeutically effective amount of the pharmaceutical composition is administered.

Yet another embodiment is a method of stimulating new bone formation in an animal or patient (such as an animal or patient in need thereof) by buccally co-administering an effective amount of a delivery agent and a PTH component. According to one embodiment, an antiresorptive agent (e.g., estrogen, selective estrogen receptor modulators, bisphosphonates, and calcitonin) is co-administered with the delivery agent and the PTH component. Preferably, a pharmaceutical composition or unitary dosage form containing all of the components is administered. A therapeutically effective amount of the components is preferably administered.

Yet another embodiment is a method of treating or preventing osteoporosis by buccally co-administering to an animal (e.g., a patient) (such as an animal in need thereof) an effective amount of (a) a delivery agent, and (b) (i) a PTH component and optionally (ii) an antiresorptive agent (such as those mentioned above). Preferably, a pharmaceutical composition or unitary dosage form containing all of the components is administered.

DETAILED DESCRIPTION OF THE INVENTION

Figure 1:
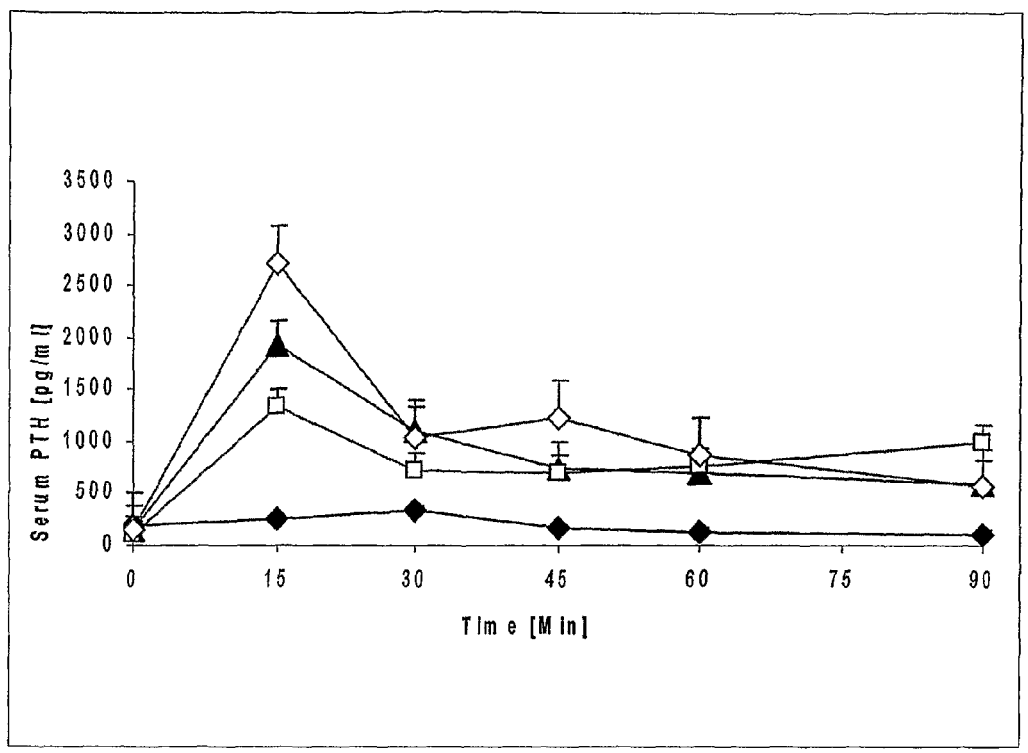
FIG. 1 is a graph of serum human parathyroid hormone (1-34) ("hPTH(1-34)") concentration over time after buccal administration of -♦-0.2 mg/kg hPTH(1-34) without a delivery agent, -▲-0.2 mg/kg hPTH(1-34) with 200 mg/kg monosodium 4-MOAC, -0-0.2 mg/kg hPTH(1-34) with 200 mg/kg monosodium SNAD, and -a-0.2 mg/kg hPTH(1-34) with 200 mg/kg monosodium 4-CNAB.

The term "substituted" as used herein includes, but is not limited to, substitution with any one or any combination of the following substituents: halogens, hydroxide, $C_1$-$C_4$ alkyl, and $C_1$-$C_4$ alkoxy.

The terms "alkyl", "alkoxy", "alkylene", "alkenylene", "alkyl(arylene)", and "aryl(alkylene)" include, but are not limited to, linear and branched alkyl, alkoxy, alkylene, alkenylene, alkyl(arylene), and aryl(alkylene) groups, respectively.

The term "delivery agent" includes, but is not limited to, any of the delivery agent compounds disclosed herein.

The term "4-MOAC" refers to 8-(N-2-hydroxy-4-methoxybenzoyl)-aminocaprylic acid and pharmaceutically acceptable salts thereof. Unless otherwise noted, the term "4-MOAC" refers to all forms of 4-MOAC, including all amorphous and polymorphic forms of 4-MOAC.

The term "NAC" as used herein refers to N-(8-[2-hydroxybenzoyl]-amino) caprylic acid and pharmaceutically acceptable salts thereof, including its monosodium salt. Unless otherwise noted, the term "NAC" refers to all forms of NAC, including all amorphous and polymorphic forms of NAC. The term "SNAC" as used herein refers to the monosodium salt of NAC, including all amorphous and polymorphic forms of SNAC (such as those described in U.S. Provisional Application No. 60/569,476, filed May 6, 2004 which is hereby incorporated by reference), unless otherwise indicated.

The term "NAD" as used herein refers to N-(8-[2-hydroxybenzoyl]-amino)decanoic acid and pharmaceutically acceptable salts thereof, including its monosodium salt. Unless otherwise noted, the term "NAD" refers to all forms of NAD, including all amorphous and polymorphic forms of NAD. The term "SNAD" as used herein refers to the monosodium salt of NAD, including all amorphous and polymorphic forms of SNAD.

The term "5-CNAC" refers to N-(8-[2-hydroxy-5-chlorobenzoyl]-amino)octanoic acid (also known as 8-(N-2-hydroxy-5-chlorobenzoyl)aminocaprylic acid)) and pharmaceutically acceptable salts thereof, including its monosodium salt. Unless otherwise noted, the term "5-CNAC" refers to all forms of 5-CNAC, including all amorphous and polymorphic forms of 5-CNAC.

The term "4-CNAB" refers to 4-[(2-hydroxy-4-chlorobenzoyl)amino]butanoate (also known as 4-[(4-chloro-2-hydroxy-benzoyl)amino]butanoic acid) and pharmaceutically acceptable salts thereof, including its monosodium salt. Unless otherwise noted, the term "4-CNAB" refers to all forms of 4-CNAB, including all amorphous and polymorphic forms of 4-CNAB. The term "sodium 4-CNAB" and "monosodium 4-CNAB" refer to monosodium 4-[(2-hydroxy-4-chlorobenzoyl)amino]butanoate, including anhydrous, monohydrate, and isopropanol solvates thereof and amorphous and polymorphic forms thereof (including those described in International Publication No. WO 03/057650 which is hereby incorporated by reference), unless otherwise indicated.

An "effective amount" of parathyroid hormone or a fragment thereof is an amount of parathyroid hormone or fragment thereof which is effective to treat or prevent a condition or to stimulate new bone formation in a living organism to whom it is administered over some period of time, e.g., provides a therapeutic effect during a desired dosing interval.

An "effective amount" of a delivery agent is an amount of the delivery agent which enables and/or facilitates the absorption of parathyroid hormone and, optionally, an antiresorptive agent when administered buccally.

An "antiresorptive agent" is an agent that reduces bone loss in an animal (such as a patient) by decreasing osteoclastic bone resorption.

The term "AUC" as used herein, means area under the plasma concentration-time curve, as calculated by the trapezoidal rule over the complete dosing interval, e.g., 24-hour interval.

The term "mean", when preceding a pharmacokinetic value (e.g., mean Peak) represents the arithmetic mean value of the pharmacokinetic value unless otherwise specified.

As used herein and in the appended claims, the singular forms "a," "an," and "the," include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

The term "patient" as used herein refers to a mammal and preferably a human.

The phrase "pharmaceutically acceptable" refers to components or compositions that are physiologically tolerable and do not typically produce an allergic or similar untoward reaction, such as gastric upset, dizziness and the like, when administered to a mammal.

The terms "buccal administration" and "buccally administering" include administration by adsorption through any surface inside the mouth or upper throat (such as the cheek (e.g., the inner cheek lining), gums, palate, tongue, tonsils, periodontal tissue, lips, and the mucosa of the mouth and pharynx). These terms, for example, include sublingual and intraoral administration.

The terms "2-OH—Ar" or "2-HO—Ar", as used in formulas 1 and 2 refer to an aryl group that is substituted with a hydroxy group at the 2 position.

Delivery Agent Compounds

Suitable delivery agents include those having the following structure and pharmaceutically acceptable salts thereof:

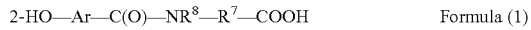

2-HO—Ar—C(O)—NR$^8$—R$^7$—COOH          Formula (1)

wherein

Ar is phenyl or naphthyl, optionally substituted with OH, halogen, $C_1$-$C_4$ alkyl, $C_1$-$C_4$ alkenyl, $C_1$-$C_4$ alkoxy or $C_1$-$C_4$ haloalkoxy;

R$^7$ is $C_4$-$C_{20}$ alkyl, $C_4$-$C_{20}$ alkenyl, phenyl, naphthyl, (Ci-$C_{10}$ alkyl) phenyl, ($C_1$-$C_{10}$ alkenyl)phenyl, ($C_1$-$C_{10}$alkyl) naphthyl, (Ci-$C_{10}$ alkenyl)naphthyl, phenyl^-Cio alkyl), phenyl(Ci-Cio alkenyl), naphthyl(Ci-$C_{10}$ alkyl), or naphthyl(Ci-Ci$_0$ alkenyl);

R$^8$ is hydrogen, Ci to $C_4$ alkyl, $C_2$ to $C_4$ alkenyl, Ci to $C_4$ alkoxy, Ci-$C_4$ or haloalkoxy;

R$^7$ is optionally substituted with $C_1$ to $C_4$ alkyl, $C_2$ to $C_4$ alkenyl, $C_1$ to $C_4$ alkoxy, $C_1$-$C_4$ haloalkoxy, —OH, —SH, and —CO$_2$R$^9$ or any combination thereof;

R$^9$ is hydrogen, $C_1$ to $C_4$ alkyl or $C_2$ to $C_4$ alkenyl; and

R$^7$ is optionally interrupted by oxygen, nitrogen, sulfur or any combination thereof;

with the proviso that the compounds are not substituted with an amino group in the position alpha to the acid group or salts thereof.

According to one embodiment, Ar is substituted with a halogen.

Preferably, R$^7$ is $C_4$-$C_{20}$ alkyl or phenyl^ —$C_{10}$ alkyl). More preferably R$^7$ is $C_5$-$C_1$Oalkyl or phenyl($C_2$ alkyl). Most preferably, R$^7$ is $C_7$-Cp alkyl or phenyl($C_2$ alkyl).

Other suitable delivery agents include those having the following structure and pharmaceutically acceptable salts thereof:

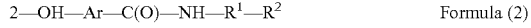

2—OH—Ar—C(O)—NH—R$^1$—R$^2$          Formula (2)

wherein

Ar is phenyl or naphthyl;

Ar is optionally substituted with $C_1$-$C_4$ alkyl, $C_1$-$C_4$ alkoxy, $C_2$-$C_4$ alkenyl, $C_2$-$C_4$ alkynyl, aryl, aryloxy, a heterocyclic ring, $C_5$-$C_7$ carbocylic ring, halogen, —OH, —SH, CO$_2$R$^6$, —NR$^7$R$^8$, Or —N$^+$H$^7$R$^8$R$^9$Y$^-$;

(a) R$^1$ is $C_1$-$C_{16}$ alkylene, $C_2$-$C_{16}$ alkenylene, $C_2$-$C_{16}$ alkynylene, $C_6$-$C_{16}$ arylene, ($C_1$-$C_{16}$ alkyl)arylene, or aryl ($C_1$-$C_{16}$ alkylene);

R$^2$ is —NR$^3$R$^4$ or —N$^+$R$^3$R$^4$R$^5$T;

R$^3$ and R$^4$ are independently hydrogen; oxygen; hydroxy; substituted or unsubstituted $C_1$-$C_{16}$ alkyl; substituted or unsubstituted $C_2$-$C_{16}$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

R$^5$ is independently hydrogen; substituted or unsubstituted $C_1$-Cj$_6$ alkyl; substituted or unsubstituted $C_2$-Ci$_6$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

(b) R$^1$, R$^2$, and R$^5$ are as defined above; and

R$^3$ and R$^4$ are combined to form a 5, 6 or 7-membered heterocyclic ring; or 5, 6 or 7-membered heterocyclic ring substituted with a $C_1$-$C_6$ alkyl, $C_1$-$C_6$ alkoxy, aryl, aryloxy, oxo group or carbocyclic ring; or (c) R$^2$ and R$^5$ are as defined above; and R$^1$ and R$^3$ are combined to form a 5, 6 or 7-membered heterocyclic ring; or 5, 6 or 7-membered heterocyclic ring substituted with a $C_1$-$C_6$ alkyl, alkoxy, aryl, aryloxy, or oxo group or carbocyclic ring;

R$^4$ is hydrogen; oxygen; hydroxy; substituted or unsubstituted $C_1$-$C_{16}$ alkyl; substituted or unsubstituted $C_2$-$C_{16}$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

R$^6$ is hydrogen; $C_1$-$C_4$ alkyl; $C_1$-$C_4$ alkyl substituted halogen or —OH; $C_2$-$C_4$ alkenyl; or $C_2$-$C_4$ alkenyl substituted halogen or —OH;

R$^7$, R$^8$, and R$^9$ are independently hydrogen; oxygen; $C_1$-$C_4$ alkyl; $C_1$-$C_4$ alkyl substituted with halogen or —OH; $C_2$-$C_4$ alkenyl; or $C_2$-$C_4$ alkenyl substituted with halogen or —OH; and Y is halogen, hydroxide, sulfate, nitrate, phosphate, alkoxy, perchlorate, tetrafluoroborate, or carboxylate. A non-limiting example of a suitable carboxylate is acetate.

The term "substituted" as used herein with respect to the compounds of formula (2) includes, but is not limited to, hydroxyl and halogen.

In one embodiment, Ar is unsubstituted phenyl or phenyl substituted with one or more Of $C_1$-$C_4$ alkyl, $C_1$-$C_4$ alkoxy, or halogen. More preferably, Ar is a phenyl substituted with methoxy, Cl, F or Br, and even more preferably, Ar is a phenyl substituted with Cl.

In another embodiment, R$^1$ is Ci-$C_{12}$ alkyl, $C_2$-$C_8$ alkyl, $C_2$-$C_6$ alkyl, or $C_6$ alkyl.

In another embodiment, $R^3$ and $R^4$ are independently H or $C_1$-$C_2$ alkyl; or further $R^3$ and $R^4$ are not both H; or further $R^3$ and $R^4$ are independently methyl or ethyl; and more preferably $R^3$ and $R^4$ are both methyl.

Other suitable delivery agents include those having the following structure and pharmaceutically acceptable salts thereof:

Formula (3)

wherein
$R^1$, $R^2$, $R^3$, and $R^4$ are independently hydrogen, —OH, —NR$^6$R$^7$, halogen, $C_1$-$C_4$ alkyl, or $C_1$-$C_4$ alkoxy;

$R^5$ is a substituted or unsubstituted $C_2$-$C_{16}$ alkylene, substituted or unsubstituted $C_2$-$C_{16}$ alkenylene, substituted or unsubstituted $C_1$-$C_{12}$ alkyl(arylene), or substituted or unsubstituted aryl($C_1$-$C_{12}$ alkylene); and $R^5$ and $R^7$ are independently hydrogen, oxygen, or $C_1$-$C_4$ alkyl.

According to one embodiment, $R^1$, $R^2$, $R^3$, and $R^4$ are H, and $R^5$ is unsubstituted $C_2$-$C_{16}$ alkylene. In one embodiment, $R^1$, $R^2$, $R^3$, and $R^4$ are H, and $R^5$ is unsubstituted $C_4$-$C_{14}$ alkylene. $R^1$, $R^2$, $R^3$, and $R^4$ are H, and $R^5$ is unsubstituted $C_6$-$C_{12}$ alkylene. In one embodiment, $R^1$, $R^2$, $R^3$, and $R^4$ are H, and $R^5$ is unsubstituted $C_6$-$C_{10}$ alkylene.

The term "substituted" as used with respect to formula (3) includes, but is not limited to, substitution with any one or any combination of the following substituents: halogens, hydroxide, $C_1$-$C_4$ alkyl, and $C_1$-$C_4$ alkoxy.

Other suitable delivery agents include those having the following structure and pharmaceutically acceptable salts thereof:

Formula (4)

wherein
(a) $R^1$, $R^2$, $R^3$, and $R^4$ are independently H, —OH, halogen, $C_1$-$C_4$ alkyl, $C_1$-$C_4$ alkenyl, $C_1$-$C_4$ alkoxy, —C(O)R$^8$, —NO$_2$, —NR$^9$R$^{10}$, or —N$^+$R$^9$R$^{10}$R$^{11}$CT);

$R^8$ is hydrogen, —OH, $C_1$-$C_6$ alkyl, $C_1$-$C_4$ alkyl substituted with halogen or —OH, $C_2$-$C_4$ alkenyl unsubstituted or substituted with halogen or —OH, or —NR$^{14}$R$^{15}$;

$R^9$, $R^{10}$, and $R^{11}$ are independently hydrogen, oxygen, $C_1$-$C_4$ alkyl unsubstituted or substituted with halogen or —OH, $C_2$-$C_4$ alkenyl unsubstituted or substituted with halogen or —OH;

Y is halide, hydroxide, sulfate, nitrate, phosphate, alkoxy, perchlorate, tetrafluoroborate, carboxylate, mesylate, fumerate, malonate, succinate, tartrate, acetate, gluconate, maleate;

$R^5$ is H, —OH, —NO$_2$, halogen, CF$_3$, —NR$^{14}$R$^{15}$, —N$^+$R$^{14}$R$^{15}$R$^{16}$(Y$^-$), amide, $C_1$-$C_{12}$ alkoxy, $C_1$-$C_{12}$ alkyl, $C_2$-$C_{12}$ alkenyl, carbamate, carbonate, urea, or —C(O)R$^{22}$; $R^5$ is optionally substituted with halogen, —OH, —SH, or —COOH; $R^5$ is optionally interrupted by O, N, S, or —C(O)—;

$R^{14}$, $R^{15}$, and $R^{16}$ are independently H or $C_1$-$C_{10}$ alkyl;
$R^{22}$ is H, $C_1$-$C_6$ alkyl, —OH, —NR$^{14}$R$^{15}$;
$R^6$ is substituted or unsubstituted $C_1$-$C_{16}$ alkylene, $C_2$-$C_{16}$ alkenylene, $C_2$-$C_{16}$ alkynylene, $C_5$-$C_{16}$ arylene, ($C_1$-$C_{16}$ alkyl)arylene or aryl($C_1$-$C_{16}$ alkylene); $R^6$ is optionally substituted with $C_1$-$C_7$ alkyl or $C_1$-$C_7$ cycloalkyl;

$R^7$ is —NR$^{18}$R$^{19}$ or —N$^+$R$^{18}$R$^{19}$R$^{20}$Y$^-$;
$R^{18}$ and $R^{19}$ are independently hydrogen, oxygen, hydroxy, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted aryl, substituted or unsubstituted alkylcarbonyl (e.g. substituted or unsubstituted ($C_{1-6}$ alkyl)carbonyl), substituted or unsubstituted arylcarbonyl, substituted or unsubstituted alkanesulfinyl (e.g. substituted or unsubstituted ($C_{1-6}$ alkane)sulfinyl), substituted or unsubstituted arylsulfinyl, substituted or unsubstituted alkanesulfonyl (e.g. substituted or unsubstituted ($C_{1-6}$ alkane)sulfonyl), substituted or unsubstituted arylsulfonyl, substituted or unsubstituted alkoxycarbonyl (e.g. substituted or unsubstituted ($C_{1-6}$ alkoxy)carbonyl), or substituted or unsubstituted aryloxycarbonyl, or substituted or unsubstituted $C_5$-$C_7$ heterocyclic ring (i.e., 5, 6, or 7-membered heterocyclic ring), wherein the substitutions may be halogen or —OH; and $R^{20}$ is independently hydrogen, substituted or unsubstituted $C_1$-$C_{16}$ alkyl, substituted or unsubstituted $C_2$-$C_6$ alkenyl, substituted or unsubstituted $C_2$-$C_{16}$ alkynyl, substituted or unsubstituted aryl, substituted or unsubstituted alkylcarbonyl (e.g. substituted or unsubstituted ($C_{1-6}$ alkyl)carbonyl), substituted or unsubstituted arylcarbonyl, substituted or unsubstituted alkanesulfinyl (e.g. substituted or unsubstituted ($C_{1-6}$ alkane)sulfinyl), substituted or unsubstituted arylsulfinyl, substituted or unsubstituted alkanesulfonyl (e.g. substituted or unsubstituted ($C_{1-6}$ alkane)sulfonyl), substituted or unsubstituted arylsulfonyl, substituted or unsubstituted alkoxycarbonyl (e.g. substituted or unsubstituted ($C_{1-6}$ alkoxy) carbonyl), or substituted or unsubstituted aryloxycarbonyl; or (b) $R^1$-$R^{16}$ and $R^{20}$ are as defined above; and
$R^{18}$ and $R^{19}$ combine to form a 5, 6, or 7-membered heterocyclic ring optionally interrupted with an oxo group and unsubstituted or substituted with $C_1$-$C_6$ alkyl, $C_1$-$C_6$ alkoxy, aryl, aryloxy, or carbocyclic ring.

According to one embodiment, $R^7$ is morpholino, morpholinium salt, or diethanolamino.

According to another embodiment, $R^6$ is a $C_1$-$C_{16}$ alkylene and $R^7$ is morpholino or a morpholinium salt. Preferably, $R^6$ is $C_4$-$C_{12}$ alkylene, such as an unsubstituted $C_4$-$C_{12}$ alkylene. More preferably, $R^6$ is $C_4$-$C_{10}$, $C_4$-$C_8$, or $C_6$-$C_8$ alkylene, such as an unsubstituted $C_4$-$C_{10}$, $C_4$-$C_8$, or $C_6$-$C_8$ alkylene. According to one embodiment, one of $R^1$-$R^5$ is hydroxy, for example, $R^1$ can be hydroxy.

According to yet another embodiment, when $R^6$ is a $C_1$-$C_{10}$ alkylene, at most one of $R^2$ and $R^4$ is halogen. According to another embodiment, $R^6$ is a $C_8$-$C_{16}$, $C_9$-$C_{16}$, $C_{10}$-$C_{16}$, or $C_{11}$-$C_{16}$ alkylene. For instance, $R^6$ may be a $C_8$, $C_9$, $C_{10}$, $C_{11}$, or $C_{12}$ alkylene (e.g., a normal $C_8$-$C_{12}$ alkylene). According to yet another embodiment, at most one of $R^1$ and $R^5$ is alkyl.

According to yet another embodiment, $R^1$ is hydroxy and $R^2$, $R^3$, $R^4$, and $R^5$ are independently hydrogen or halogen.

According to yet another embodiment, $R^2$ is hydroxy and $R^1$, $R^3$, $R^4$, and $R^5$ are independently hydrogen or halogen.

According to yet another embodiment, $R^3$ is hydroxy and $R^1$, $R^2$, $R^4$, and $R^5$ are independently hydrogen or halogen.

In a preferred embodiment, halogen is F, Cl or Br, more preferably F or Cl, and even more preferably Cl.

According to yet another embodiment, $R^6$ is $Ci$-$Ci_6$ alkylene, ($C_1$-$C_{16}$ alkyl) arylene or aryl($C_1$-$C_{16}$ alkylene). More preferably $R^6$ is $C_1$-$Ci_2$ alkylene, more preferably $C_3$-$Ci_0$ alkylene, more preferably $C_4$-$C_{10}$ or $C_4$-$C_8$ alkylene, and more preferably $C_6$-$C_8$ alkylene. More preferably, $R^6$ is unsubstituted.

According to yet another embodiment, $R^7$ is —$NR^{18}R^{19}$ and $R^{18}$ and $R^{19}$ are independently $C_1$-$C_4$ alkyl (e.g., methyl, ethyl, propyl, or butyl) substituted with —OH. In another embodiment, $R^7$ is —$NR^{18}R^{19}$ and $R^{18}$ and $R^{19}$ combine to form a six membered heterocyclic ring substituted with an oxo group.

According to one preferred embodiment, $R^1$ is hydrogen; $R^2$, $R^3$, and $R^4$ are independently hydrogen, halogen, —OH, or —$OCH_3$; $R^5$ is hydrogen, —OH, or —$C(O)CH_3$; $R^6$ is $C_1$-$C_{12}$ alkylene, and $R^7$ is $NR^{18}R^{19}$ wherein $R^{18}$ and $R^{19}$ combine to form a 5, 6, or 7 membered heterocyclic ring.

According to another preferred embodiment, one of $R^3$, $R^4$, and $R^5$ is hydroxy and the others are independently halogen or hydrogen; $R^1$ and $R^2$ are independently halogen or hydrogen; $R^6$ is $C_1$-$C_{16}$ alkylene; and $R^7$ is $NR^{18}R^{19}$ wherein $R^{18}$ and $R^{19}$ combine to form a 5, 6, or 7 membered heterocyclic ring. $R^6$ is preferably $C_6$-$C_{16}$, $C_6$-$Ci_0$, $C_8$-$C_{16}$, $C_{10}$-$C_{16}$, or $C_4$-$C_8$ alkylene, such as unsubstituted $C_6$-$Ci_6$, $C_6$-$C_{10}$, $C_8$-$C_{16}$, $C_{10}$-$Ci_6$, or $C_4$-$C_8$ alkylene. Preferably, $R^{18}$ and $R^{19}$ form a morpholino or imidazole.

In another preferred embodiment, $R^1$ is hydrogen; $R^2$, $R^3$, and $R^4$ are independently hydrogen, halogen, —OH, Or —$OCH_3$; $R^5$ is hydrogen, —$OH_5$ or —$C(O)CH_3$; $R^6$ is $Ci$-$C_{12}$ alkylene; and $R^7$ is $N^4R^{18}R^{19}R^{20}$ ($Y^-$) wherein $R^{18}$ and $R^{19}$ are hydroxy substituted $C_1$-$C_{16}$ alkyl and $R^{20}$ is hydrogen.

In another preferred embodiment, $R^1$ is hydrogen; $R^2$, $R^3$, and $R^4$ are independently hydrogen, halogen, —OH, or —$OCH_3$; $R^5$ is hydrogen, —OH, or —$C(O)CH_3$; $R^6$ is $C_1$-$C_{12}$ alkylene; and $R^7$ is $N^+R^{18}R^{19}R^{20}$ ($Y^-$) wherein $R^8$ and $R^{19}$ are hydroxy substituted $C_1$-$C_{16}$ alkyl and $R^{20}$ is hydrogen.

In another preferred embodiment, $R^1$, $R^2$, $R^4$, $R^5$ are independently halogen or hydrogen; $R^3$ is —OH, or —$OCH_3$; and $R^7$ is $N^+R^{18}R^{19}R^{20}$ ($Y^-$) wherein $R^{18}$ and $R^{19}$ are hydroxy substituted $C_1$-$Ci_6$ alkyl and $R^{20}$ is hydrogen.

According to one preferred embodiment, $R^1$ is hydrogen; $R^2$, $R^3$, and $R^4$ are independently hydrogen, halogen, —OH, or —$OCH_3$; $R^5$ is hydrogen, —OH, or —$C(O)CH_3$; $R^6$ is $C_1$-$C_6$alkylene or aryl substituted $C_1$-$C_{12}$ alkyl; and $R^7$ is —$NR^{18}R^{19}$ wherein $R^{18}$ and $R^{19}$ combine to form a 5, 6, or 7 membered heterocyclic ring or $N^+R^{18}R^{19}R^{20}$ ($Y^-$) wherein $R^{18}$ and $R^{19}$ are hydroxy substituted $C_1$-$C_{16}$ alkyl and $R^{20}$ is hydrogen.

In another preferred embodiment, the citrate salt of the delivery agent is used.

Other suitable delivery agents include those having the following structure and pharmaceutically acceptable salts thereof:

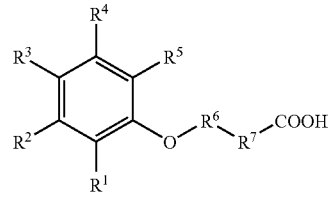

Formula (5)

wherein
$R^1$, $R^2$, $R^3$, and $R^4$ are independently H, —$OH_5$ halogen, $C_1$-$C_4$ alkyl, $C_2$-$C_4$ alkenyl, $C_1$-$C_4$ alkoxy, —$C(O)R^8$, —$NO_2$, —$NR^9R^{10}$, or —$N^+R^9R^{10}R^{11}(R^{12})^-$;

$R^5$ is H, —OH, —$NO_2$, halogen, —$CF_3$, —$NR^{14}R^{15}$, —$N^+R^{14}R^{15}R^{16}(R^{13})^-$, amide, $C_1$-$C_{12}$ alkoxy, $C_1$-$C_{12}$ alkyl, $C_2$-$C_{12}$ alkenyl, carbamate, carbonate, urea, or —$C(O)R^{18}$;

$R^5$ is optionally substituted with halogen, —OH, —SH, or —COOH;

$R^5$ is optionally interrupted by O, N, S, or —C(O)—;

$R^6$ is a $C_1$-$C_{12}$ alkylene, $C_2$-$C_{12}$ alkenylene, or arylene;

$R^6$ is optionally substituted with a $C_1$-$C_4$ alkyl, $C_2$-$C_4$ alkenyl, $C_1$-$C_4$ alkoxy, —OH, —SH, halogen, —$NH_2$, or —$CO_2R^8$;

$R^6$ is optionally interrupted by O or N;

$R^7$ is a bond or arylene;

$R^7$ is optionally substituted with —OH, halogen, —$C(O)CH_3$, —$NR^{10}R^{11}$, or —$N^+R^{10}R^{11}R^{12}$ ($R^{13}$)—;

$R^8$ is H, $C_1$-$C_4$ alkyl, $C_2$-$C_4$ alkenyl, or —$NH_2$;

$R^9$, $R^{10}$, $R^{11}$, and $R^{12}$ independently H or $C_1$-$C_{10}$ alkyl;

$R^{13}$ is a halide, hydroxide, sulfate, tetrafluoroborate, or phosphate; and $R^{14}$, $R^{15}$ and $R^{16}$ are independently H, $C_1$-$C_{10}$ alkyl, $Ci$-$C_{10}$ alkyl substituted with —$COOH_5C_2$-$C_{12}$ alkenyl, $C_2$-$C_{12}$ alkenyl substituted with —COOH, —$C(O)R^{17}$;

$R^{17}$ is —OH, $C_1$-$C_{10}$ alkyl, or $C_2$-$C_{12}$ alkenyl; and $R^{18}$ is H, $C_1$-$C_6$ alkyl, —OH, —$NR^{14}R^{15}$, Or $N^+R^{14}R^{15}R^{16}$ ($R^{13}$).

According to one embodiment,
(1) when $R^1$, $R^2$, $R^3$, $R^4$, and $R^5$ are H, and $R^7$ is a bond then $R^6$ is not a $C_1$-$C_6$, $C_9$ or $C_{10}$ alkyl;
(2) when $R^1$, $R^2$, $R^3$, and $R^4$ are H, $R^5$ is —OH, $R^7$ is a bond then $R^6$ is not a $C_1$-$C_3$ alkyl;
(3) when at least one of $R^1$, $R^2$, $R^3$, and $R^4$ is not H, $R^5$ is —OH, $R^7$ is a bond, then $R^6$ is not a $C_1$-$C_4$ alkyl;
(4) when $R^1$, $R^2$, and $R^3$ are $H_5R^4$ is —$OCH_3$, $R^5$ is —$C(O)CH_3$, and $R^6$ is a bond then $R^7$ is not a $C_3$ alkyl; and
(5) when $R^1$, $R^2$, $R^4$, and $R^5$ are H, $R^3$ is —OH, and $R^7$ is a bond then $R^6$ is not a methyl.

According one preferred embodiment, $R^1$ is hydrogen; $R^2$, $R^3$, and $R^4$ are independently hydrogen, halogen, —OH, or —$OCH_3$; $R^5$ is hydrogen, —OH, or —$C(O)CH_3$; $R^6$ is $C_1$-$C_{12}$ alkylene, and $R^7$ is a bond or para-phenylene. $R^7$ is more preferably a $C_7$-$C_9$ alkyl.

According to another preferred embodiment, at least one of $R^1$, $R^2$, $R^3$, and $R^4$ is hydrogen, —$C(O)CH_3$, —$OH_5Cl_5$—$OCH_3$, F, or —$NO_2$. In one more preferred embodiment, $R^2$ is —$C(O)CH_3$, —$OH_5$—$OCH_3$, or —Cl. In another more preferred embodiment, $R^3$ is Cl, —$OCH_3$, $F_5$ or —OH. In yet another more preferred embodiment, $R^4$ is —$OCH_3$ or —$NO_2$.

According to yet another preferred embodiment, $R^5$ is —$C(O)CH_3$, —OH, H, —CH=$CHCH_3$, —$NH_2$, —$NO_2$, —$NHC(O)CH_3$, —CH=$CHCO_2H$, —$C(O)CH_2CH_3$, —$C(O)NH_2$, —$C(O)NHCH_3$, —COOH, —C(O)

NHCH$_2$CH$_3$, —C(O)NHCH(CH$_3$)$_2$, —OCH$_3$, —C(CH$_3$)$_2$OH, —C(OH)(CH$_3$)$_2$, or —CH(OH)CH$_3$.

According to yet another preferred embodiment, R$^6$ is a linear C$_1$-C$_{12}$ alkylene. More preferably, R$^6$ is -(CH$_2$)$_n$—, where n is an integer from 1 to 10.

According to yet another preferred embodiment, R$^4$ and R$^5$ are not alkyl or halogen.

According to yet another preferred embodiment, R$^7$ is para-phenylene or a bond.

According to yet another preferred embodiment, R$^6$ is —CH$_2$— and R$^7$ is phenylene and, more preferably para-phenylene. More preferably, at least one of R$^1$, R$^2$, R$^3$, and R$^4$ is hydrogen. More preferably, R$^5$ is —C(O)CH$_3$, —OH or —C(CH$_3$)$_2$OH.

According to yet another preferred embodiment, R$^7$ is a bond, R$^5$ is —OH, and R$^1$, R$^2$, R$^3$, and R$^4$ are hydrogen. R$^6$ is preferably C$_4$-C$_{12}$ alkylene and, more preferably, C$_4$-C$_9$ alkylene.

According to yet another preferred embodiment, R$^7$ is a bond, R$^5$ is —OH, and at least one of R$^1$, R$^2$, R$^3$, and R$^4$ is not hydrogen. R$^6$ is preferably C$_1$-C$_{12}$ alkylene, more preferably Cs-C$_{12}$ alkylene, and most preferably C$_5$-C$_9$ alkylene.

According to yet another preferred embodiment, R$^7$ is a bond, R$^5$ is —C(O)CH$_3$, and R$^1$, R$^2$, R$^3$, and R$^4$ are hydrogen. R$^6$ is preferably Ci-C$_{12}$ alkylene, more preferably C$_3$-Ci$_2$ alkylene, and most preferably C$_3$-C$_7$ alkylene.

According to yet another preferred embodiment, R$^7$ is a bond and R$^1$, R$^2$, R$^3$, R$^4$ and R$^5$ are hydrogen. Preferably, R$^6$ is C$_7$-C$_8$ alkylene.

According to yet another preferred embodiment, R$^7$ is a bond, R$^5$ is hydrogen, and at least one R$^1$, R$^2$, R$^3$, and R$^4$ are not hydrogen. R$^6$ is preferably Ci-C$_{12}$ alkylene, more preferably C$_4$-C$_9$ alkylene, and most preferably C$_7$-C$_8$ alkylene.

According to yet another preferred embodiment, R$^2$ is —OH. More preferably, R$^7$ is a bond and R$^5$ is hydrogen. Preferably, R$^5$ is Ci-C$_{12}$ alkylene, more preferably C$_3$-C$_9$ alkylene, and most preferably C$_7$ alkylene.

According to yet another preferred embodiment, R$^3$ is —OH. More preferably, R$^7$ is a bond and R$^5$ is hydrogen. R$^6$ is preferably C$_1$-C$_{12}$ alkylene, more preferably C$_3$-C$_9$ alkylene, and most preferably C$_7$ alkylene.

Other suitable delivery agents include those having the following structure and pharmaceutically acceptable salts thereof:

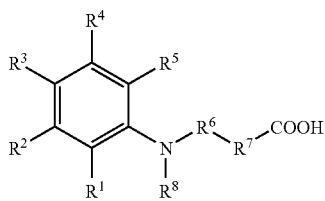

Formula (6)

wherein
R$^1$, R$^2$, R$^3$, and R$^4$ are independently H, —OH, halogen, —OCH$_3$, —NR$^{10}$R$^{11}$ or —N$^+$R$^{10}$R$^{11}$R$^{12}$(R$^{13}$)—;
R$^5$ is H, —OH, —NO$_2$, —NR$^{14}$R$^{15}$, —N$^+$R$^{14}$R$^{15}$R$^{16}$(R$^{13}$)", amide, C$_1$-C$_{12}$ alkoxy, C$_1$-Ci$_2$ alkyl, C$_2$-Ci$_2$ alkenyl, carbamate, carbonate, urea, or —C(O)R$^{18}$;
R$^5$ is optionally substituted with —OH, —SH, or —COOH;
R$^5$ is optionally interrupted by O, N, S, or —C(O)—;
R$^6$ is a Ci-C$_{12}$ alkylene, Ci-Ci$_2$ alkenylene, or arylene;

R$^6$ is optionally substituted with a Ci-C$_4$ alkyl, C$_2$-C$_4$ alkenyl, CpC$_4$ alkoxy, —OH, —SH, halogen, —NH$_2$, or —CO$_2$R$^9$;
R$^6$ is optionally interrupted by O or N;
R$^7$ is a bond or arylene;
R$^7$ is optionally substituted with —OH, halogen, —C(O)CH$_{35}$—NR$^{10}$R$^{11}$ or —N$^+$R$^{10}$R$^{11}$R$^{12}$ (R$^{13}$)$^-$;
R$^8$ is H or C$_1$-C$_4$ alkyl;
R$^9$ is H, Ci-C$_4$ alkyl, or C$_2$-C$_4$ alkenyl;
R$^{10}$, R$^{11}$, and R$^{12}$ are independently H or C$_1$-Ci$_0$ alkyl;
R$^{13}$ is a halide, hydroxide, sulfate, tetrafluoroborate, or phosphate;
R$^{14}$, R$^{15}$, and R$^{16}$ are independently H, Ci-Ci$_0$ alkyl, C$_2$-Ci$_2$ alkenyl, O, or —C(O)R$^{17}$;
R$^{17}$ is —OH, Ci-Cio alkyl, or C$_2$-Ci$_2$ alkenyl; and
R$^{18}$ is —OH, Ci-C$_6$ alkyl, —NR$^{14}$R$^{15}$, —N$^+$R$^{14}$R$^{15}$R$^{16}$(R$^{13}$)\

According to one embodiment, when R$^5$ is OCH$_3$ then R$^6$ is C$_1$-C$_8$ or C$_{10}$-C$_{12}$ alkyl.

According to a preferred embodiment, R$^5$ is not —OCH$_3$. More preferably, R$^5$ is not alkoxy.

According to another preferred embodiment, R$^1$, R$^2$, R$^3$, and R$^4$ are hydrogen, R$^5$ is —COOH, —C(O)NH$_2$, —C(O)CH$_3$, or —NO$_2$, R$^6$ is —(CH$_2$)$_7$—, and R$^7$ is a bond.

According to yet another preferred embodiment, R$^1$, R$^2$, R$^3$, and R$^4$ are hydrogen, R$^5$ is —C(O)NH$_2$, R$^6$ is —CH$_2$—, and R$^7$ is a para-phenylene.

According to one embodiment, the delivery agents of formula (6) have the formula:

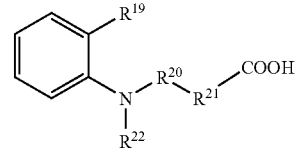

Formula (7)

wherein
R$^{19}$ is —NO$_2$ or —C(O)R$^{23}$;
R$^{20}$ is a C$_1$-C$_{12}$ alkylene or C$_1$-C$_{12}$ alkenylene;
R$^{21}$ is a bond or arylene;
R$^{22}$ is H or C$_1$-C$_4$ alkyl; and
R$^{23}$ is —OH, C$_1$-C$_6$ alkyl, or —NH$_2$.

Preferred delivery agents include, but are not limited to, NAC (including SNAC), NAD (including SNAD), 5-CNAC, 4-MOAC, 4-CNAB, and pharmaceutically acceptable salts thereof. In one embodiment, the delivery agent is SNAC. In one embodiment, the delivery agent is a di-sodium salt of NAC. In one embodiment, the delivery agent is SNAD.

Other suitable delivery agents of the present invention are described in U.S. Pat. Nos. 6,699,467, 6,663,898, 6,693,208, 6,693,073, 6,693,898, 6,663,887, 6,646,162, 6,642,411, 6,627,228, 6,623,731, 6,610,329, 6,558,706, 6,525,020, 6,461,643, 6,461,545, 6,440,929, 6,428,780, 6,413,550, 6,399,798, 6,395,774, 6,391,303, 6,384,278, 6,375,983, 6,358,504, 6,346,242, 6,344,213, 6,331,318, 6,313,088, 6,245,359, 6,242,495, 6,221,367, 6,180,140, 6,100,298, 6,100,285, 6,099,856, 6,090,958, 6,084,112, 6,071,510, 6,060,513, 6,051,561, 6,051,258, 6,001,347, 5,990,166, 5,989,539, 5,976,569, 5,972,387, 5,965,121, 5,962,710, 5,958,451, 5,955,503, 5,939,381, 5,935,601, 5,879,681, 5,876,710, 5,866,536, 5,863,944, 5,840,340, 5,824,345, 5,820,881, 5,811,127, 5,804,688, 5,792,451, 5,776,888, 5,773,647, 5,766,633, 5,750,147, 5,714,167, 5,709,861, 5,693,338, 5,667,806, 5,650,386, 5,643,957, 5,629,020, 5,601,846, 5,578,323, 5,541,155, 5,540,939, 5,451,410, 5,447,728, 5,443,841, and 5,401,516. Delivery agents of the present invention are also described in U.S. Published Application Nos. 200401 10839, 20040106825, 20040068013, 20040062773, 20040022856, 20030235612, 20030232085, 20030225300, 20030198658, 20030133953, 20030078302, 20030072740, 20030045579, 20030012817, 20030008900, 20020155993, 20020127202, 20020120009, 20020119910, 20020102286, 20020065255, 20020052422, 20020040061, 20020028250, 20020013497, 20020001591, 20010039258, and 20010003001. Delivery agents of the present invention are also described in International Publication Nos. WO 2004/4104018, WO 2004080401, WO 2004062587, WO 2003/057650, WO 2003/057170, WO 2003/045331, WO 2003/045306, WO 2003/026582, WO 2002/100338, WO 2002/070438, WO 2002/069937, WO 02/20466, WO 02/19969, WO 02/16309, WO 02/15959, WO 02/02509, WO 01/92206, WO 01/70219, WO 01/51454, WO 01/44199, WO 01/34114, WO 01/32596, WO 01/32130, WO 00/07979, WO 00/06534, WO 00/06184, WO 00/59863, WO 00/59480, WO 00/50386, WO 00/48589, WO 00/47188, WO 00/46182, WO 00/40203, WO 99/16427, WO 98/50341, WO 98/49135, WO 98/34632, WO 98/25589, WO 98/21951, WO 97/47288, WO 97/31938, WO 97/10197, WO 96/40076, WO 96/40070, WO 96/39835, WO 96/33699, WO 96/30036, WO 96/21464, WO 96/12475, and WO 9612474. Each of the above listed U.S. patents and U.S. and International published applications are herein incorporated by reference.

The delivery agent compounds depicted as carboxylic acids may be in the form of the carboxylic acid or salts thereof. Suitable salts include, but are not limited to, organic and inorganic salts, for example alkali-metal salts, such as sodium (e.g., monosodium and disodium salts), potassium and lithium; alkaline-earth metal salts, such as magnesium, calcium or barium; ammonium salts; basic amino acids, such as lysine or arginine; and organic amines, such as dimethylamine or pyridine. Preferably, the salts are sodium salts. The salts may be mono- or multi-valent salts, such as monosodium salts and di-sodium salts. The salts may also be solvates, including ethanol solvates, and hydrates.

The delivery agent compounds depicted as amines may be in the form of the free amine or salts thereof. Suitable salts include, but are not limited to, organic and inorganic salts, for example sodium salts, sulfate salts, hydrochloride salts, phosphate salts, fluoride salts, carbonate salts, tartrate salts, oxalates, oxides, formates, acetate or citrate.

Salts of the delivery agent compounds of the present invention may be prepared by methods known in the art. For example, sodium salts may be prepared by dissolving the delivery agent compound in ethanol and adding aqueous sodium hydroxide.

Where the delivery agent has an amine moiety and a carboxylic acid moiety, poly amino acids and peptides comprising one or more of these compounds may be used. An amino acid is any carboxylic acid having at least one free amine group and includes naturally occurring and synthetic amino acids. Poly amino acids are either peptides (which are two or more amino acids joined by a peptide bond) or are two or more amino acids linked by a bond formed by other groups which can be linked by, e.g., an ester or an anhydride linkage. Peptides can vary in length from dipeptides with two amino acids to polypeptides with several hundred amino acids. One or more of the amino acids or peptide units may be acylated or sulfonated.

The delivery agent may contain a polymer conjugated to it such as described in International Publication No. WO 03/045306. For example, the delivery agent and polymer may be conjugated by a linkage group selected from the group consisting of —NHC(O)NH—, —C(O)NH—, —NHC(O), —OOC—, —COO—, —NHC(O)O—, —OC(O)NH—, —CH$_2$NH—NHCH$_2$—, —CH$_2$NHC(O)O—, —OC(O) NHCH$_2$—CH$_2$NHCOCH$_2$O—, OCH$_2$C(O)NHCH$_2$—^NHC (O)CH$_2$O—, —OCH$_2$C(O)NH—, —NH—, —O—, and carbon-carbon bond, with the proviso that the polymeric delivery agent is not a polypeptide or polyamino acid. The polymer may be any polymer including, but not limited to, alternating copolymers, block copolymers and random copolymers, which are safe for use in mammals.

Preferred polymers include, but are not limited to, polyethylene; polyacrylates; polymethacrylates; poly (oxyethylene); poly (propylene); polypropylene glycol; polyethylene glycol (PEG); and derivatives thereof and combinations thereof. The molecular weight of the polymer typically ranges from about 100 to about 200,000 daltons. The molecular weight of the polymer preferably ranges from about 200 to about 10,000 daltons. In one embodiment, the molecular weight of the polymer ranges from about 200 to about 600 daltons and more preferably ranges from about 300 to about 550 daltons.

The compounds described herein may be derived from amino acids and can be readily prepared from amino acids by methods within the skill of those in the art, such as those described in International Publication Nos. WO 96/30036, WO 97/36480, WO 00/06534, WO 00/46812, WO 00/50386, WO 00/59863, WO 01/32596, WO 01/92206, and WO 00/07979 and U.S. Pat. Nos. 5,643,957, 5,650,386, and 5,866,536, all of which are incorporated by reference. For example, the compounds may be prepared by reacting the single amino acid with the appropriate acylating or amine-modifying agent, which reacts with a free amino moiety present in the amino acid to form amides. Protecting groups may be used to avoid unwanted side reactions as would be known to those skilled in the art. With regard to protecting groups, reference is made to T. W. Greene, *Protecting Groups in Organic Synthesis*, Wiley, New York (1981), the disclosure of which is hereby incorporated herein by reference.

The delivery agent compound may be purified by recrystallization or by fractionation on one or more solid chromatographic supports, alone or linked in tandem. Suitable recrystallization solvent systems include, but are not limited to, acetonitrile, methanol, ethanol, ethyl acetate, heptane, water, tetrahydrofuran, and combinations thereof. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

Parathyroid Hormone (PTH) Component

Any form of parathyroid hormone known in the art may be used. Suitable forms of parathyroid hormone components include, but are not limited to, mammalian parathyroid hormone, e.g. human (hPTH), bovine (bPTH), and porcine (pptH), and fragments and analogs thereof. The parathyroid hormone component can be the full length, 84 amino acid form of parathyroid hormone, e.g., the human form, hPTH (1-84), or any polypeptide, protein, protein fragment, or modified fragment, i.e. PTH-related peptides and PTH analogs, capable of mimicking the activity of hPTH (1-84) in controlling calcium and phosphate metabolism to build bone in the human body.

According to one embodiment, the PTH fragments incorporate at least the first 28 N-terminal residue (such as a PTH fragment selected from PTH (1-28) to PTH (1-41)). Examples of such PTH fragments include, but are not limited to, PTH (1-28), PTH (1-31), PTH (1-34), PTH (1-37), PTH (1-38), PTH (1-41), hPTH (1-28), hPTH (1-31), hPTH (1-34), cyclical hPTH (1-34), hPTH (1-37), hPTH (1-38), hPTH (1-41), and analogs thereof, such as PTS893. Other suitable forms of PTH are described in U.S. Pat. Nos. 4,086,196, 5,208,041, 5,814,603, 5,171,670, Re. 37,919, and 5,510,370 and U.S. Patent Application Publication Nos. 2004-0186050 and 2004-0242478, all of which are hereby incorporated by reference.

According to another embodiment, the hPTH fragments include at least the first 28 N-terminal residues (PTH (1-28)) up to and including the first 41 N-terminal residues (PTH (1-41) ) and include without limitation PTH (1-28), PTH (1-31), PTH (1-34), PTH (1-37), PTH (1-38) and PTH (1-41). A preferred PTH fragment is hPTH (1-34).

The PTH component can be a single type of PTH or a combination of two or more types of PTH. The PTH components are generally commercially available or can be obtained recombinantly, by peptide synthesis, or by extraction from human fluid by methods known in the art.

The amount of PTH to be administered is generally a therapeutically effective amount. For example, the amount can be that effective to treat or prevent osteoporosis in the animal or to stimulate new bone formation in an animal. This amount may vary with the age, size, sex and condition of the animal to be treated, the nature and severity of the disorder to be treated. The total amount of PTH to be used can be determined by methods known to those skilled in the art. According to one embodiment, from about 0.001 µg/kg to about 10 mg/kg animal body weight, from about 0.01 µg/kg to about 1 mg/kg body weight or from about 0.1 µg/kg to about 0.5 mg/kg body weight of the PTH component is administered.

Antiresorptive Agents

Without being bound by any particular theory, it is believed that antiresorptive agents reduce bone loss by decreasing osteoclastic bone resorption and may result in an increase in bone mineral density (BMD). Examples of antiresortive agents include, but are not limited to, bisphosphonates, a steroid hormone (e.g., estrogen, a partial estrogen agonist or estrogen-gestagen combination), a SERM (selective estrogen receptor modulator) (e.g., raloxifene, lasofoxifene, TSE-424, FC1271, Tibolone (Livial®), vitamin D or an analogue thereof), calcitonin, and mixtures thereof. Examples of bisphosphonates include, but are not limited to, alendronate, ibandronate, zoledronate, risedronate, tiludronate, etidronate, clodronate, pamidronate, olpadronate, and incadronate (including their free acid and salt forms). The hormone estrogen may be administered as a means of increasing BMD or may be supplemented by a selective estrogen receptor modulator such as raloxifene (available as Evista™ from Eli Lilly & Co. of Indianapolis, Ind.).

A preferred antiresorptive agent is calcitonin. Calcitonin may be either natural, synthetic, or recombinant, including, but no limited to, salmon, pig, eel, and human calcitonin. Calcitonin derivatives, such as 1,7-Asn-eel calcitonin, can also be used. A preferred calcitonin is salmon calcitonin. According to one embodiment, the buccal pharmaceutical composition includes calcitonin and a PTH component as described in U.S. Patent Application Publication No. 2004-0186050, which is hereby incorporated by reference. According to U.S. Patent Application Publication No. 2004-0186050, the calcitonin negates the hypercalcemic effect of the PTH while attaining the same reduction in serum calcium obtained when calcitonin is administered alone, in the absence of PTH. The calcitonin/PTH pharmaceutical compositions may be administered to treat Paget's disease, hypercalcemia (including hypercalcemia of malignancy) and osteoporosis. The appropriate dosage of calcitonin to be administered will, of course, vary depending upon, for example, the amount of PTH to be administered and the severity of the condition being treated. According to one embodiment, calcitonin is administered at daily dosages of from about 0.5 µg/kg to about 10 µg/kg animal body weight, preferably 1 µg/kg to about 6 µg/kg body weight.

Pharmaceutical Compositions

The composition of the present invention comprises one or more delivery agents of the present invention and a PTH component. The delivery agent(s) and PTH are typically mixed prior to administration to form an administration composition.

The administration compositions may be in the form of a liquid dosage form. The solution medium may be water, 25% aqueous propylene glycol, or phosphate buffer. Other dosing vehicles include polyethylene glycol. Dosing solutions may be prepared by mixing a solution of the delivery agent compound with a solution of the active agent, just prior to administration. Alternately, a solution of the delivery agent (or PTH) may be mixed with the solid form of PTH (or the delivery agent). The delivery agent and PTH may also be mixed as dry powders. The delivery agent compound and PTH can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging from about 0.1 and 20% (w/v).

The administration compositions may alternately be in the form of a solid, such as a tablet, capsule or particle, such as a powder or sachet. Solid dosage forms may be prepared by mixing the solid form of the compound with the solid form of the PTH component. Alternately, a solid may be obtained from a solution of the delivery agent compound and the PTH component by methods known in the art, such as freeze-drying (lyophilization), precipitation, crystallization and solid dispersion. Alternatively, the administration can be a semi-solid, in the form of a gel, paste, colloid, gelatin, emulsion, suspension and the like.

The administration compositions of the present invention may also include one or more antiresorptive agents (including those described above).

Preferably the compositions of the present invention are administered buccally. Without being bound by any particular theory, applicants believe that there is less dilution and fewer food effects when the PTH component is absorbed buccally. Buccal administration can also provide a sustained (flat) release profile, which is helpful, for example, to prevent subjects from eating over a longer time period.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

Dosage unit forms for buccal administrations may contain ingredients known to facilitate buccal administration. The buccal dosage unit form, for example, may be formulated so as to erode gradually over a predetermined time period and release PTH and delivery agent at a constant or substantially constant rate. According to one embodiment, the time period ranges from about 0.5 hours to about 24 hours. A bioerodible (hydrolyzable) polymeric carrier that adheres the dosage form to the buccal mucosa, such as that described in U.S.

Published Patent Application No. 2003/0134861 (which is hereby incorporated by reference), can be used, e.g., to provide a sustained release profile. Suitable bioerodible (hydrolyzable) polymeric carriers include, but are not limited to, those which provide a sustained release profile and are compatible with PTH.

According to one embodiment, the polymeric carrier comprises hydrophilic (water-soluble and water-swellable) polymers that adhere to the wet surface of the buccal mucosa. Non-limiting examples of polymeric carriers useful herein include acrylic acid polymers, e.g., those known as "carbomers" (Carbopol®, which may be obtained from B. F. Goodrich is one such polymer). Other suitable polymers include, but are not limited to: hydrolyzed polyvinylalcohol; polyethylene oxides (e.g., Sentry Polyox® water soluble resins, available from Union Carbide of Midland, Mich.); polyacrylates (e.g., Gantrez®, which may be obtained from GAF of Wayne, N.J.); vinyl polymers and copolymers; polyvinylpyrrolidone; dextran; guar gum; pectins; starches; and cellulosic polymers such as hydroxypropyl methylcellulose (e.g., Methocel®, which may be obtained from the Dow Chemical Company of Midland, Mich.), hydroxypropyl cellulose (e.g., Klucel®, which may also be obtained from Dow), hydroxypropyl cellulose ethers (see, e.g., U.S. Pat. No. 4,704,285 to Alderman), hydroxyethyl cellulose, carboxymethyl cellulose, sodium carboxymethyl cellulose, methyl cellulose, ethyl cellulose, cellulose acetate phthalate, cellulose acetate butyrate, and the like.

Other components may also be incorporated into the buccal dosage forms described herein. The additional components include, but are not limited to, disintegrants, diluents, binders, lubricants, flavoring, colorants, preservatives, and the like. Non-limiting examples of disintegrants are cross-linked polyvinylpyrrolidones, such as crospovidone (e.g., Polyplasdone® XL, which may be obtained from GAF), cross-linked carboxylic methylcelluloses, such as croscarmelose (e.g., Ac-di-sol®, which may be obtained from FMC Corporation of Philadelphia, Pa.), alginic acid, and sodium carboxymethyl starches (e.g., Explotab®, which may be obtained from Edward Medell Co., Inc.), methylcellulose, agar bentonite and alginic acid. Suitable diluents include, but are not limited to, those which are generally useful in pharmaceutical formulations prepared using compression techniques, e.g., dicalcium phosphate dihydrate (e.g., Di-Tab®, which may be obtained from Stauffer), sugars that have been processed by cocrystallization with dextrin (e.g., co-crystallized sucrose and dextrin such as Di-Pakg, which may be obtained from Amstar), lactone, calcium phosphate, cellulose, kaolin, mannitol, sodium chloride, dry starch, powdered sugar and the like. Suitable binders include, but are not limited to, those that enhance adhesion. Non-limiting examples of such binders are starch, gelatin and sugars such as sucrose, dextrose, molasses, and lactose. Non-limiting examples of lubricants include, but are not limited to, stearates (e.g., magnesium stearate) and stearic acid.

Preferred sublingual dosage forms include sublingual tablets, creams, ointments and pastes. The tablet, cream, ointment or paste for sublingual delivery comprises a therapeutically effective amount of PTH and one or more conventional nontoxic carriers suitable for sublingual drug administration. The sublingual dosage forms of the present invention can be manufactured using conventional processes. The sublingual dosage unit is fabricated to disintegrate rapidly. The time period for complete disintegration of the dosage unit is typically in the range of from about 10 seconds to about 30 minutes, and optimally is less than about 5 minutes.

Other components may also be incorporated into the sublingual dosage forms described herein. The additional components include, but are not limited to, binders, disintegrators, wetting agents, lubricants, and the like. Examples of binders that may be used include water, ethanol, polyvinyl pyrrolidone, and starch solution gelatin solution. Suitable disintegrators include, but are not limited to, dry starch, calcium carbonate, polyoxyethylene sorbitan fatty acid esters, sodium lauryl sulfate, stearic monoglyceride, and lactose. Wetting agents, if used, include glycerin, and starches. Suitable lubricants include but are not limited to, stearates and polyethylene glycol. Additional components that may be incorporated into sublingual dosage forms include those known in the art; such as those described in *Remington's, The Science and Practice of Pharmacy*, (Gennaro, A. R., ed., 20th edition, 2003, Mack Pub. Co.) which is herein incorporated by reference.

One or more of a solvent, an optional cosolvent, a hydrogel, and an oral mucosal membrane transport enhancing agent, such as those described in U.S. Pat. No. 5,284,657 (which is hereby incorporated by reference), may be included in the dosage unit form for buccal administration. The solvent may comprise from about 50 percent w/v to about 95 percent w/v or from about 55 percent w/v to about 80 percent w/v of a carrier of a non-toxic alcohol. Suitable non-toxic alcohols include, but are not limited to, ethanol, isopropanol, stearyl alcohol, propylene glycol, and polyethylene glycol (e.g., those having a molecular weight of up to about 650 daltons). Non-toxic alcohols for use in pharmaceutical formulations are well known in the art (cf., for example, *Handbook of Pharmaceutical Excipients*, published by the American Pharmaceutical Association and The Pharmaceutical Society of Great Britain (1986), which is hereby incorporated by reference in its entirety).

The cosolvent may be selected from water or a pharmaceutically acceptable oil. Suitable oils for use in the unit dosage form of this invention include mineral oil, Neobee™ oil, olive oil, sunflower oil, corn oil, peanut oil and the like. Hydrogels suitable for use in the dosage unit form include hydroxypropyl cellulose, hydroxypropyl methyl cellulose, sodium carboxymethylcellulose (CMC), polyacrylic acid, and poly(methyl methacrylic acid).

Typically, the oral mucosal membrane transport enhancing agent facilitates the absorption of the therapeutic agent (e.g., PTH) across the mucosal tissues in the oral cavity and directly into the blood stream of the subject. Suitable tissue transport enhancing agents include, but are not limited to, pharmaceutically acceptable and non-toxic essential oils, volatile oils, inorganic acids, and organic acids.

Essential or volatile oils which may be employed in the compositions include, but are not limited to, peppermint oil, spearmint oil, menthol, pepper oil, eucalyptus oil, cinnamon oil, ginger oil, fennel oil, and dill oil. The essential or volatile oil, when employed as the oral mucosal membrane transport enhancing agent in the dosage unit form may be present in a concentration ranging between about 0.5 percent w/v and 50 percent w/v of the carrier.

Suitable inorganic and organic acids include, but are not limited to, hydrochloric acid, phosphoric acid, aromatic and aliphatic monocarboxylic or dicarboxylic acids of from two to thirty carbon atoms such as acetic acid, citric acid, lactic acid, oleic acid, linoleic acid, lauric acid, palmitic acid, benzoic acid, and salicylic acid. As used in this paragraph, the term "aromatic" carboxylic acid refers to any acid which contains the 6-membered carbocyclic ring system characteristic of benzene, and the term "aliphatic" carboxylic acid refers to any acid which contains a straight-chain or branched chain saturated or unsaturated hydrocarbon backbone.

Liquid compositions for buccal administration can be formulated into a liquid spray, a liquid drop, a gel or a paste. The desired consistency can be achieved by including in the liquid composition one or more hydrogels, substances that absorb water and produce gels of varying viscosity. Hydrogels suitable for use in pharmaceutical preparations include those known well known in the art, such as those described in *Handbook of Pharmaceutical Excipients*, supra, and *Handbook of Water-Soluble Gums and Resins*, ed. by R. L. Davidson, McGraw-Hill Book Co., New York, N.Y. (1980) (both of which are hereby incorporated by reference).

Suitable hydrogels for use in the compositions of this invention include hydroxypropyl cellulose, hydroxypropyl methyl cellulose, sodium carboxymethyl cellulose, polyacrylic acid, poly(methyl methacrylic acid) (PMMA). Preferred hydrogels are cellulose ethers such as hydroxyalkylcellulose (e.g., hydroxypropyl cellulose) and hydroxyalkylalkyl-cellulose compounds. Hydroxypropyl cellulose is commercially available in a wide range of viscosity grades sold under the tradename Klucel™ (Hercules, Ltd., London, England). The concentration of the hydroxyalkylcellulose is dependent upon the particular viscosity grade used and the desired viscosity of the liquid composition. For example, where the desired viscosity is less than about 1000 centipoise (cps), hydroxypropyl cellulose having an average molecular weight of about 60,000 daltons (i.e., Klucel EF™) can be used. Where the desired viscosity is from about 1000 to about 2500 cps, higher viscosity grades of hydroxypropyl cellulose can be used (e.g., Klucel LF™ and Lucel GF™).

The dosage unit form for buccal administration may also include collagen, a water soluble additive, and/or other pharmaceutical additives, such as those described in U.S. Pat. No. 5,496,559. Collagen includes, for example, atelocollagen which is derived from a natural resource, and which is free of a telopeptide which is an antigenic portion of collagen; chemically modified atelocollagen; and naturally-occurring collagen. The collagen which has been chemically derived from the atelocollagen includes, for example, a succinylated collagen and a methylated collagen. The naturally-occurring collagen includes, for example, a collagen from a skin of bovine, a chorda of bovine, a bowel of porcine and sheep, and a human placenta. The collagen can contain a buffer, such as phosphate buffer, citrate buffer, and acetate buffer, and/or a stabilizer. Water soluble additives include for example, proteins, glycoproteins, amino acids, polyamino acids, peptides, saccharides, water-soluble polysaccharides, or a combination thereof. Proteins include, for example, gelatin and albumin. Glycoproteins include, for example, globulin. Amino acids include, for example, aspartic acid, arginine, glycine, and leucine. Polyamino acids and peptides include, for example, polyalanine, polyglycine, sodium polygultamate, sodium polyaspartate, polylysine, and polyleucine. Saccharides, polysaccharides, and water-soluble polysaccharides include, for example, fructose, sucrose, lactose, dextran, cyclodextrin, mannitol, and sorbitol. A stabilizer includes one which is used for the proteinaceous physiologically active substances, such as albumin, gelatin, mannitol, and trehalose. Suitable preservatives include, but are not limited to, p-hydroxybenzoates, sorbic acid, and salicylic acid. Suitable buffers include, but are not limited to, citrate buffer, acetate buffer, and phosphate buffer. Suitable sweeteners include, but are not limited to, mannitol, glucose, maltose, starch, and lactose. Suitable flavors include, but are not limited to, aspartic acid, citric acid, and lactic acid. Suitable binder include, but are not limited to, methylcellulose, ethylcellulose, and carboxy methyl cellulose. Suitable suspending agents include, but are not limited to, Tween 20 and Tween 80. Suitable disintegrators include, but are not limited to, glycerol and starch.

Dosage unit forms for buccal administration may be in the form of a hard candy (e.g. lollipops and mints) or a film, e.g., a slow dissolving film or a fast dissolving film (such as that described in U.S. Pat. No. 6,596,298, which is hereby incorporated by reference). Such films can be prepared by including a film forming agent in the dosage unit form. Suitable film forming agents include, but are not limited to, those described in U.S. Pat. No. 6,596,298 (e.g., pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof. According to one embodiment, the concentration of film forming agent in the dosage unit form ranges from about 0.01 to about 99 wt %, from about 30 to about 80 wt %, from about 45 to about 70 wt %, or from about 60 to about 65 wt % (based upon 100% total weight of the film). Administration compositions can also take the form of a pouch that can be placed next to the cheek, or between the lower teeth and lip, similar to smoke-less tobacco products.

The compounds and compositions of the subject invention are useful for administering biologically or chemically active agents to any animals, including but not limited to insects, birds such as chickens; fish, reptiles, mammals, such as rodents, cows, pigs, dogs, cats, primates, and particularly humans.

EXAMPLES

The following examples illustrate the invention without limitation. All parts are given by weight unless otherwise indicated.

Example 1

Buccal Administration of PTH

PTH (1-34) was administered to rats bucally with and without a delivery agent. The buccal dosage of PTH used was 0.2 mg/kg body weight. The dose of delivery agent was 200 mg/kg body weight.

A stock solution of human recombinant PTH (1-34) was prepared by dissolving hPTH (1-34) (Eli Lilly, Indianapolis, Ind.) in deionized water to a concentration of 4 mg/ml. A stock solution of delivery agent was prepared by dissolving the delivery agent in deionized water. The pH of the resulting delivery agent solution was adjusted to between 7.5 and 8.5. A liquid buccal dosage form was prepared by mixing the PTH stock solution with the delivery agent stock solution immediately prior to dosing. For the present example, four dosage forms were prepared as described below.

| Dose No. | Delivery Agent | Delivery Agent Dose | PTH Dose |
|---|---|---|---|
| 1 | Monosodium 4-MOAC | 200 mg/kg | 0.2 mg/kg |
| 2 | Monosodium 4-CNAB | 200 mg/kg | 0.2 mg/kg |
| 3 | SNAD | 200 mg/kg | 0.2 mg/kg |
| 4 | — | — | 0.2 mg/kg |

The dosage forms were administered to Male Sprague Dawley rats, ranging in weight from about 250 g to about 200 g. Each rat was anesthesized with 2% isofiurane in pure oxygen during the whole experiment. The femoral artery was cannulated for blood sampling. The esophagus was ligated to prevent wallowing of the dosing solution. The trachea was intubated and the rat was provided with a constant flow of 2% isofiurane in oxygen.

The liquid dosage form was administered by inserting a T-shaped dosing tool into the mouth of the rat. The center of the dosing tool was placed under the tongue and the liquid dosage form (approximately 05 ml/kg body weight) was administered by syringe through the dosing tool, such that the dosage was distributed evenly throughout the buccal area. Following administration, the mouth was glued shut. Blood samples were drawn at predetermined periods from the femoral artery and assayed for PTH. The liquid dosage solution was allowed to remain in the buccal area for 90 minutes (e.g., the dosing duration). After 90 minutes the liquid dosage solution was removed from the buccal area by syringe.

The concentration of PTH was determined using a PTH (1-34) immunradiometric assay kit (Immutopics, San Clemente, Calif.). Samples were prepared by storage for 20 minutes between 2° C. and 8° C., followed by centrifugation at 10,000 G for 10 minutes to obtain serum. The serum concentration of PTH was than determined using a PTH (1-34) immunradiometric assay kit.

The results of buccal administration of PTH with each of the delivery agents of the present example are shown in FIG. 1.

Example 2

Buccal Administration of PTH and 4-MOAC

A liquid dosage solution of PTH and the delivery agent monosodium 4-MOAC was prepared as described above. Three different dosage solutions were prepared, each having a different concentration of delivery agent. The three dosage solutions are described below.

| Dose No. | Delivery Agent | Delivery Agent Dose | PTH Dose |
|---|---|---|---|
| 1 | Monosodium 4-MOAC | 50 mg/kg | 0.05 mg/kg |
| 2 | Monosodium 4-MOAC | 100 mg/kg | 0.05 mg/kg |
| 3 | Monosodium 4-MOAC | 200 mg/kg | 0.05 mg/kg |

The liquid dosage forms were administered to rats as described above. The dosing duration was 5 minutes, after which time the liquid dosage form was removed from the buccal area by syringe. The serum concentration of PTH was determined as described above.

Figure 2:
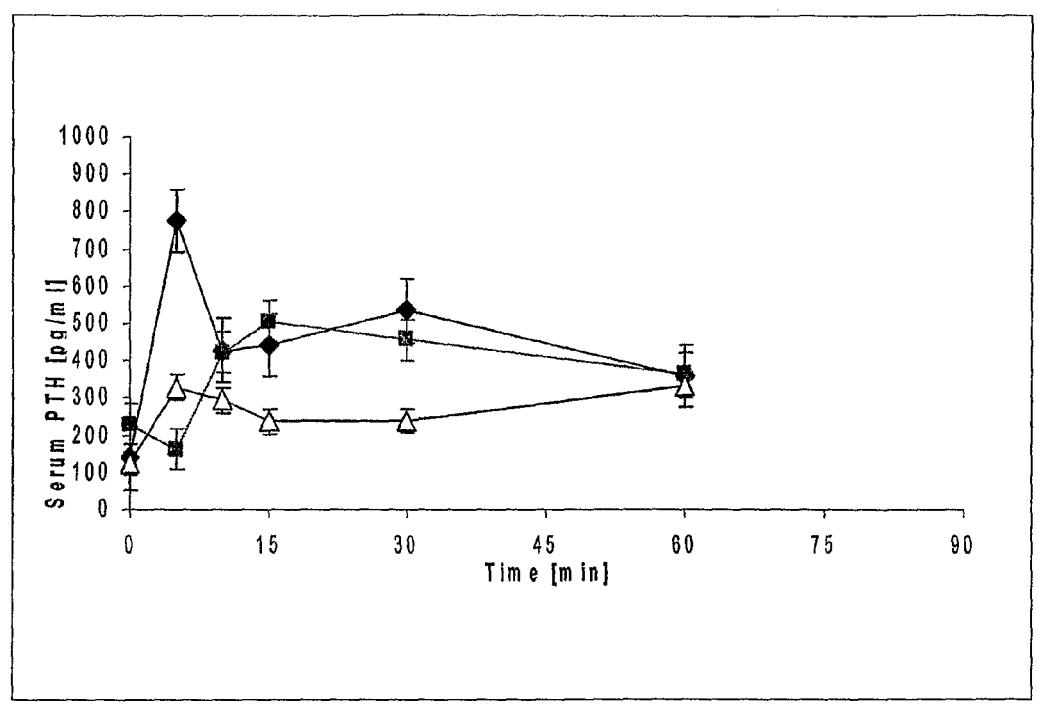
FIG. 2 is a graph of serum hPTH(1-34) concentration over time after buccal administration of -♦-0.05 mg/kg hPTH(1-34) with 50 mg/kg 4-MOAC, -■-0.05 mg/kg hPTH(1-34) with 100 mg/kg monosodium 4-MOAC, and -Δ-0.05 mg/kg hPTH(1-34) with 200 mg/kg monosodium 4-MOAC, for a dosing duration of 5 minutes.

The results of buccal administration of PTH with different concentrations of delivery agent are shown in FIG. 2.

The effect of the dosing amount of delivery agent on buccal administration was examined by preparing three dosage solutions, each having a different concentration of delivery agent. A liquid dosage solution of PTH and the delivery agent monosodium 4-MOAC was prepared as described above. Three different dosage solutions were prepared, each having a different concentration of PTH. The three dosage solutions are described below.

| Dose No. | Delivery Agent | Delivery Agent Dose | PTH Dose |
|---|---|---|---|
| 1 | Monosodium 4-MOAC | 50 mg/kg | 0.2 mg/kg |
| 2 | Monosodium 4-MOAC | 100 mg/kg | 0.2 mg/kg |
| 3 | Monosodium 4-MOAC | 200 mg/kg | 0.2 mg/kg |

The liquid dosage forms were administered to rats as described above. The dosing duration was 5 minutes, after which time the liquid dosage form was removed from the buccal area by syringe. The serum concentration of PTH was determined as described above.

Figure 3:
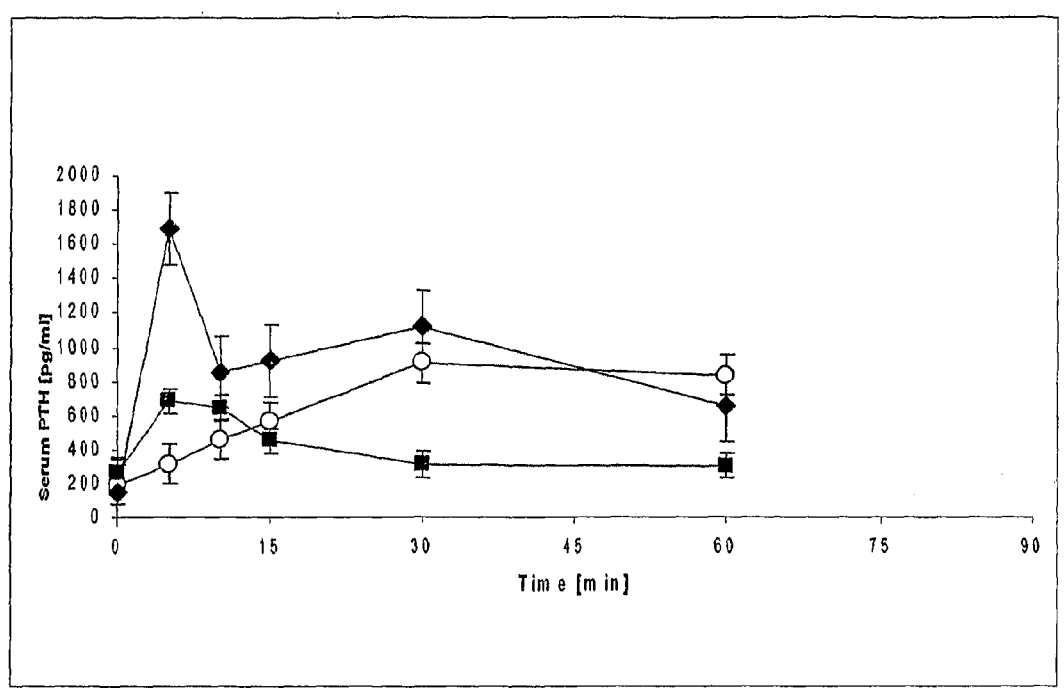
FIG. 3 is a graph of serum hPTH(1-34) concentration over time after buccal administration of -♦-0.2 mg/kg hPTH(1-34) with 200 mg/kg monosodium 4-MOAC, -■-0.2 mg/kg hPTH(1-34) with 100 mg/kg monosodium 4-MOAC, and -o-0.2 mg/kg hPTH(1-34) with 50 mg/kg monosodium 4-MOAC, for a dosing duration of 5 minutes.

The results of buccal administration of PTH with different concentrations of PTH are shown in FIG. 3.

The effect of the dosing amount of PTH on buccal administration was examined by preparing four addition dosage solutions, each having a different concentration of PTH. A liquid dosage solution of PTH and the delivery agent monosodium 4-MOAC was prepared as described above. Four different dosage solutions were prepared, each having a different concentration of PTH. The four dosage solutions are described below.

| Dose No. | Delivery Agent | Delivery Agent Dose | PTH Dose |
|---|---|---|---|
| 1 | Monosodium 4-MOAC | 100 mg/kg | 0.05 mg/kg |
| 2 | Monosodium 4-MOAC | 100 mg/kg | 0.1 mg/kg |
| 3 | Monosodium 4-MOAC | 100 mg/kg | 0.2 mg/kg |
| 4 | Monosodium 4-MOAC | 100 mg/kg | 0.3 mg/kg |

The liquid dosage forms were administered to rats as described above. The dosing duration was 5 minutes, after which time the liquid dosage form was removed from the buccal area by syringe. The serum concentration of PTH was determined as described above.

Figure 4:
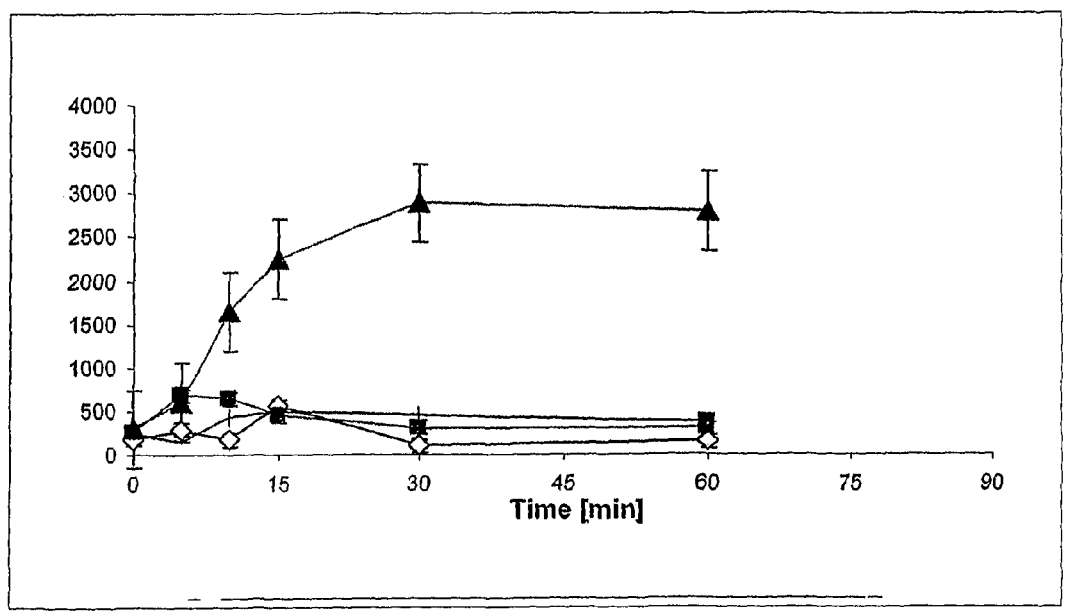
FIG. 4 is a graph of serum hPTH (1-34) concentration over time after buccal administration of -▲-0.3 mg/kg hPTH(1-34) with 100 mg/kg monosodium 4-MOAC, -■-0.2 mg/kg hPTH(1-34) with 100 mg/kg monosodium 4-MOAC, -Δ-with 0.1 mg/kg hPTH(1-34) with 100 mg/kg monosodium 4-MOAC, and –0.05 mg/kg hPTH(1-34) with 100 mg/kg monosodium 4-MOAC, for a dosing duration of 5 minutes.

The results of buccal administration of PTH with different concentrations of delivery agent are shown in FIG. 4.

Figure 5:
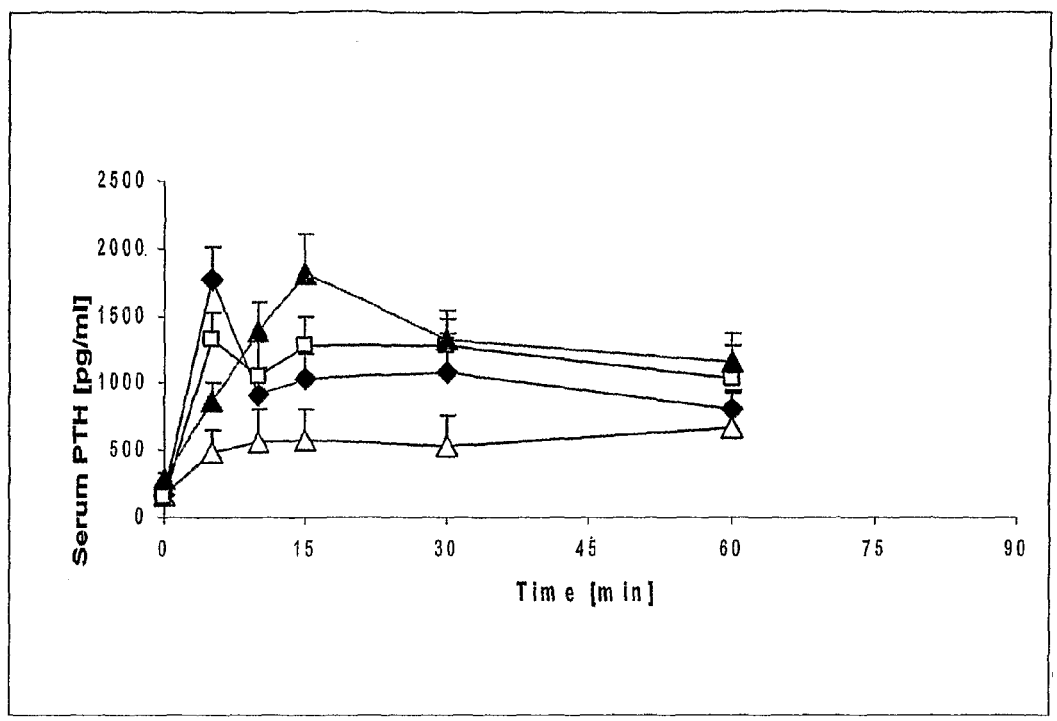
FIG. 5 is a graph of serum human parathyroid hormone (1-34) concentration over time after buccal administration of 0.2 mg/kg hPTH(1-34) with 200 mg/kg monosodium 4-MOAC over a dosing duration of 2 minutes (-Δ-), 5 minutes (-♦-), 15 minutes (-□-), and 60 minutes (-▲-).

To further investigate the buccal administration of PTH, an experiment was designed varying the dosing duration. A liquid dosage form was prepared as described above wherein the dosage amount of monosodium 4-MOAC was 200 mg/kg and the dosage amount of PTH was 0.2 mg /kg. The dosing duration was varied between 2 and 60 minutes, with the liquid dosage being removed by syringe at the end of each dosing period. The liquid dosage form was administered as described above and serum concentration of PTH was determined as described previously. The results of the varied dosing duration are shown in FIG. 5.

Example 3

Buccal Versus Oral Administration of PTH

Figure 6:
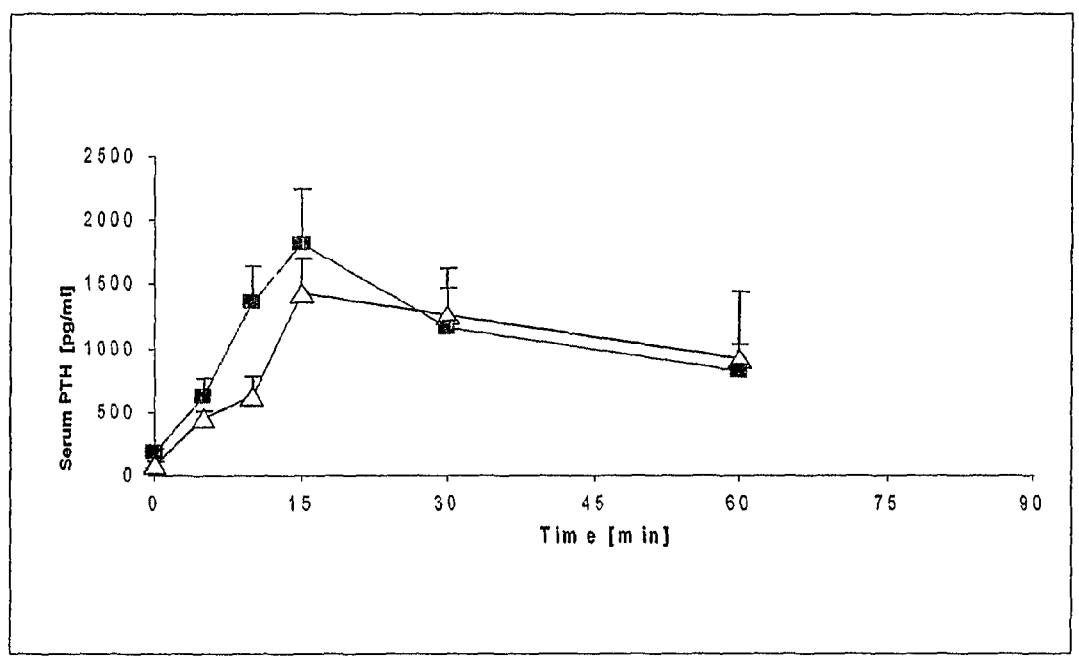
FIG. 6 is a graph of serum hPTH(1-34) concentration over time after -■-buccal administration of 0.2 mg/kg hPTH(1-34) with 200 mg/kg monosodium 4-MOAC for a dosing duration of 60 minutes and -Δ-oral administration of 0.2 mg/kg hPTH(1-34) with 200 mg/kg monosodium 4-MOAC.
Figure 7:
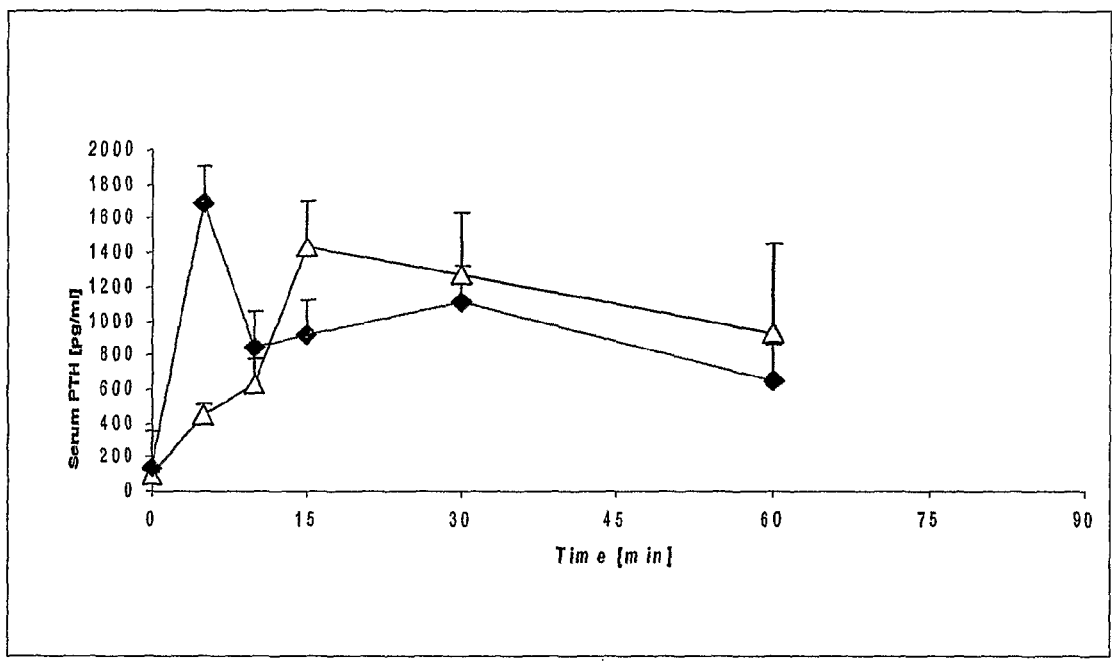
FIG. 7 is a graph of serum hPTH(1-34) concentration overtime after -■-buccal administration of 0.2 mg/kg hPTH(1-34) with 200 mg/kg monosodium 4-MOAC for a dosing duration of 5 minutes and -Δ-oral administration of 0.2 mg/kg PTH with 200 mg/kg monosodium 4-MOAC.

A liquid dosage form was prepared as described above wherein the dosage amount of monosodium 4-MOAC was 200 mg/kg and the dosage amount of PTH was 0.2 mg/kg. The dosage form was administered buccally as described above. Oral administration was carried out by anesthetizing the rat with a mixture of ketamine (44 mg/kg) and thorazine (1.5 mg/kg), followed by administration of the oral dosage by a gavaging trocar. The dosing duration for buccal administration was 5 and 60 minutes respectively. Blood samples were drawn from the rat as described above and the serum concentration of PTH was determined as described previously. The resulting serum concentration of PTH is shown in FIGS. 6 and 7. The resulting pharmacokinetic data for oral and buccal administration is shown in Table 1, below.

TABLE 1

Pharmacokinetic Data for Oral and Buccal Administration

|  | $C_{max}$ (pg/ml) | $T_{max}$ (min) | $AUC_{0 \to t}$ (pg/ml min) | Buccal:Oral $AUC_{0 \to t}$ Ratio | $AUC_{0 \to \infty}$ (pg/ml min) | Buccal:Oral $AUC_{0 \to \infty}$ Ratio |
|---|---|---|---|---|---|---|
| Oral | 1432 | 15 | 623453 | — | 157151 | — |
| Buccal (5 min dosing duration) | 1702 | 5 | 58498 | 0.94 | 168141 | 1.1 |
| Buccal (60 min dosing duration) | 1817 | 15 | 77213 | 1.2 | 206657 | 1.3 |

Example 4

Buccal Administration of PTH in Dogs

The animal was moderately sedated using 0.4-0.8 mg/kg midazolam (IM) and 0.03-0.04 mg/kg medetomidine IV or IM in order to minimize the risk of the animal swallowing the test material. The level of sedation was continuously monitored and respiratory rate and general activity level was noted. Once adequately sedated, the dog was moved to a flat surface and an intravenous catheter was placed in the cephalic vein. For dose application, the dog was placed on its side with its head and jaw angled to maximally hold the test material in the mouth.

For an aqueous dosing solution, a syringe filled with the dosing solution (up to 1.5 ml) was placed sublingually and infused slowly up to 0.75 ml in an equal amount at the right and left space under the tongue of the dog. For sublingual tablet, the tablets were placed under the tongue and up to 1.5 ml of saline was administered to facilitate the sublingual dissolution. On one hour post-administration, any remaining formulation was removed by syringe aspiration and the area was rinsed once with saline solution and the saline solution that was then removed by a syringe aspiration.

Once the animal recovered from the sedatives, restraint-acclimated animals was restrained using a sling for the duration of the experiment. Blood samples were collected at specific time-points, i.e., 0, 0.25, 0.5, 1, 1.5, 2, 2.5 and up to 4 hours.

For comparison of the dosing route with intraoral delivery, an oral tablet dosing study was followed. The equivalent dose of drug and carrier was prepared to be the oral formulation of tablets that were gavaged, and 1 ml of water was administered into the gavaging tubing.

TABLE 2

Pharmacokinetic Data for Administration of PTH to Dogs

|  | No. Samples | $C_{max}$ (pg/ml) | $T_{max}$ (min) | $AUC_{0 \to t}$ (pg/ml min) | $AUC_{0 \to t}$ BA (%) | $AUC_{0 \to t}$ CV (%) |
|---|---|---|---|---|---|---|
| Buccal | 8 | 3345 ± 2652 | 62 ± 39 | 169167 ± 11800 | 3.3 | 69.8 |
| Oral | 4 | 632 ± 568 | 23 ± 9 | 24572 ± 14060 | 4.8 | 57.2 |
| Subcutaneous | 4 | 6391 ± 1969 | 26 ± 8 | 508117 ± 138966 | 100 | 27.3 |

The final two columns in Table 2 show the relative bioavailability to subcutaneous administration by buccal and oral administrations of PTH to dog, and the respective coefficient of variations.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application, the disclosures of which are incorporated herein by reference in their entireties for all purposes.

What is claimed is:

1. A pharmaceutical composition for administration through the cheek lining comprising (a) a delivery agent selected from 4-MOAC, and pharmaceutically acceptable salts thereof, and (b) a parathyroid hormone component, wherein the composition is free of calcitonin.

2. The composition of claim 1, wherein the delivery agent is a monosodium salt of 4-MOAC.

3. A method for preventing or treating osteoporosis in a patient in need thereof comprising administering through the cheek lining an effective amount of a pharmaceutical composition comprising (a) a delivery agent selected from 5-CNAC, 4-MOAC, and pharmaceutically acceptable salts thereof, and (b) a parathyroid hormone component, wherein the composition is free of calcitonin.

4. A method of stimulating new bone formation in a patient comprising administering through the cheek lining an effective amount of a pharmaceutical composition comprising (a) a delivery agent selected from 5-CNAC, 4-MOAC, and pharmaceutically acceptable salts thereof, and (b) a parathyroid hormone component, wherein the composition is free of calcitonin.

5. A method for treating hypoparathyroidism in a patient in need thereof comprising administering through the cheek lining an effective amount of a pharmaceutical composition comprising (a) a delivery agent selected from 5-CNAC, 4-MOAC, and pharmaceutically acceptable salts thereof, and (b) a parathyroid hormone component, wherein the composition is free of calcitonin.

6. The method of claim 3, wherein the delivery agent is 5-CNAC, or a pharmaceutically acceptable salt thereof.

7. The method of claim 4, wherein the delivery agent is 5-CNAC, or a pharmaceutically acceptable salt thereof.

8. The method of claim 5, wherein the delivery agent is 5-CNAC, or a pharmaceutically acceptable salt thereof.

9. The method of claim 6, wherein the delivery agent is a monosodium salt of 5-CNAC.

10. The method of claim 7, wherein the delivery agent is a monosodium salt of 5-CNAC.

11. The method of claim 8, wherein the delivery agent is a monosodium salt of 5-CNAC.

* * * * *